United States Patent
Schifano et al.

(10) Patent No.: US 9,119,732 B2
(45) Date of Patent: Sep. 1, 2015

(54) METHOD AND IMPLANT SYSTEM FOR SACROILIAC JOINT FIXATION AND FUSION

(71) Applicant: Orthocision, Inc., Folsom, CA (US)

(72) Inventors: Troy Schifano, Las Vegas, NV (US); Steve Anderson, Folsom, CA (US); Gowriharan Thaiyananthan, Irvine, CA (US)

(73) Assignee: Orthocision, Inc., Folsom, CA (US)

( * ) Notice: Subject to any disclaimer, the term of this patent is extended or adjusted under 35 U.S.C. 154(b) by 17 days.

(21) Appl. No.: 13/842,227

(22) Filed: Mar. 15, 2013

(65) Prior Publication Data
US 2014/0277460 A1     Sep. 18, 2014

(51) Int. Cl.
*A61F 2/44*  (2006.01)
*A61F 2/46*  (2006.01)
*A61B 17/17* (2006.01)
*A61B 17/16* (2006.01)
(Continued)

(52) U.S. Cl.
CPC ........... *A61F 2/4611* (2013.01); *A61B 17/1757* (2013.01); *A61F 2/447* (2013.01); *A61F 2/4455* (2013.01); *A61B 17/1671* (2013.01); *A61B 17/7055* (2013.01); *A61F 2002/30785* (2013.01); *A61F 2002/30828* (2013.01); *A61F 2002/30904* (2013.01); *A61F 2002/30995* (2013.01)

(58) Field of Classification Search
CPC ....... A61F 2/4455; A61F 2/4611; A61F 2/46; A61F 2002/30995
USPC ............................ 623/17.11, 18.11, 902, 908
See application file for complete search history.

(56) References Cited

U.S. PATENT DOCUMENTS

| | | | |
|---|---|---|---|
| 5,334,205 A | * | 8/1994 | Cain .............................. 606/96 |
| 5,741,261 A | | 4/1998 | Moskovitz et al. |
| 6,053,916 A | | 4/2000 | Moore |

(Continued)

FOREIGN PATENT DOCUMENTS

| | | |
|---|---|---|
| WO | 2006074422 A1 | 7/2006 |
| WO | 2011087912 A1 | 7/2011 |

(Continued)

OTHER PUBLICATIONS

Globus Medical Inc., Description of SI-LOK® Sacroiliac Fixation System, available online at www.globusmedical.com.
(Continued)

*Primary Examiner* — Jerry Cumberledge
*Assistant Examiner* — Tessa Matthews
(74) *Attorney, Agent, or Firm* — Mark D. Miller; William K. Nelson

(57) ABSTRACT

An improved method of implanting a bone graft in a joint and tools for accomplishing the same is disclosed. The present invention relates generally to tools and methods useful for treating a sacroiliac joint. In one embodiment, the present invention is a method including the steps of: creating a first incision in the patient's skin proximal to the patient's sacroiliac joint; creating an incision in the patient's skin over the patient's ilium; inserting a first working channel into said first incision and spreading said sacroiliac joint with an inserted end of said first working channel; inserting a second working channel into said second incision and forming a hole in said ilium; creating a void in said sacroiliac joint; inserting a graft into said void; and inserting a joint fusing device into said ilium and said sacrum.

64 Claims, 21 Drawing Sheets

(51) Int. Cl.
*A61B 17/70* (2006.01)
*A61F 2/30* (2006.01)

(56) References Cited

U.S. PATENT DOCUMENTS

| | | | |
|---|---|---|---|
| 6,440,444 B2 | 8/2002 | Boyce et al. | |
| 6,635,059 B2 | 10/2003 | Randall et al. | |
| 6,695,844 B2 | 2/2004 | Bramlet | |
| 7,648,509 B2 | 1/2010 | Stark | |
| 7,731,981 B2 | 6/2010 | Trieu | |
| 7,744,651 B2 | 6/2010 | Trieu | |
| 7,993,347 B1 | 8/2011 | Michelson | |
| 8,162,981 B2 | 4/2012 | Vestgaarden | |
| 8,202,305 B2 | 6/2012 | Reiley | |
| 8,221,428 B2 | 7/2012 | Trieu | |
| 8,308,779 B2 | 11/2012 | Reiley | |
| 8,343,189 B2 | 1/2013 | Assell et al. | |
| 8,348,950 B2 | 1/2013 | Assell et al. | |
| 8,388,667 B2 | 3/2013 | Reiley et al. | |
| 8,852,241 B2 * | 10/2014 | Datta | 606/279 |
| 2004/0054414 A1 | 3/2004 | Trieu | |
| 2004/0215203 A1 | 10/2004 | Michelson | |
| 2004/0228901 A1 | 11/2004 | Trieu | |
| 2005/0119754 A1 | 6/2005 | Trieu | |
| 2006/0054171 A1 | 3/2006 | Dall | |
| 2006/0089646 A1 | 4/2006 | Bonutti | |
| 2007/0134343 A1 | 6/2007 | Trieu | |
| 2007/0270879 A1 * | 11/2007 | Isaza et al. | 606/104 |
| 2008/0009861 A1 * | 1/2008 | Stark | 606/61 |
| 2008/0154275 A1 | 6/2008 | Assell et al. | |
| 2009/0036927 A1 | 2/2009 | Vestgaarden | |
| 2009/0076551 A1 | 3/2009 | Peterson | |
| 2009/0099610 A1 * | 4/2009 | Johnson et al. | 606/86 R |
| 2010/0106194 A1 | 4/2010 | Bonutti | |
| 2010/0268228 A1 | 10/2010 | Petersen | |
| 2011/0009869 A1 * | 1/2011 | Marino et al. | 606/87 |
| 2011/0060375 A1 | 3/2011 | Bonutti | |
| 2011/0098817 A1 * | 4/2011 | Eckhardt et al. | 623/17.11 |
| 2011/0166575 A1 * | 7/2011 | Assell et al. | 606/79 |
| 2011/0172494 A1 | 7/2011 | Bass et al. | |
| 2011/0184518 A1 | 7/2011 | Trieu | |
| 2011/0184519 A1 | 7/2011 | Trieu | |
| 2011/0230966 A1 * | 9/2011 | Trieu | 623/17.12 |
| 2011/0238181 A1 | 9/2011 | Trieu | |
| 2011/0264229 A1 | 10/2011 | Donner | |
| 2012/0022535 A1 | 1/2012 | Mayer et al. | |
| 2012/0083883 A1 * | 4/2012 | Ginn | 623/17.11 |
| 2012/0095560 A1 | 4/2012 | Donner | |
| 2012/0116454 A1 * | 5/2012 | Edidin et al. | 606/247 |
| 2012/0143334 A1 | 6/2012 | Boyce et al. | |
| 2012/0191191 A1 | 7/2012 | Trieu | |
| 2012/0253398 A1 | 10/2012 | Metcalf et al. | |
| 2012/0296428 A1 * | 11/2012 | Donner | 623/17.11 |
| 2013/0018427 A1 | 1/2013 | Pham et al. | |
| 2013/0035723 A1 | 2/2013 | Donner | |
| 2013/0144343 A1 * | 6/2013 | Arnett et al. | 606/279 |
| 2014/0336763 A1 * | 11/2014 | Donner et al. | 623/17.11 |

FOREIGN PATENT DOCUMENTS

| | | | |
|---|---|---|---|
| WO | 2011091349 A2 | | 7/2011 |
| WO | WO 2011087912 | * | 7/2011 |
| WO | 2012174485 A1 | | 12/2012 |
| WO | 2013043584 A2 | | 3/2013 |

OTHER PUBLICATIONS

Medtronic Inc., Description of Infuse Bone Graft/LT-Cage Lumbar Tapered Fusion Device, available online at www.medtronic.com.
Minsurg Corporation, Description of TruFUSE® Procedure, available online at www.minsurg.com.
Orthopedic Designs North America, Inc., Description of Talon® DistalFix® Femoral Nail System, available online at www.odi-na.com.
Osteotech, Inc., Description of Xpanse® R Bone Insert, available at www.osteotech.com.
Signus Medizintechnik GMBH, Description of the DIANA system, available online at www.si-joint.net.
Medtronic Sofamor Danek, Inc., 510(k) premarket notification of intent to market MSB Sacroiliac Joint Fusion Device and response letter from the Department of Health and Human Services, available online at http://sijpain.com/wp-content/uploads/K110472.pdf.
Tedan Surgical Innovations, Description of Phantom TL Transverse Retractor Frame with locking conical connection, available online at www.tedansurgical.com.
VG Innovations, LLC, Description of the SiJoin™ sacroiliac implant, available online at www.vginnovations.com.
Zyga Technology, Inc., Description of the SImmetry® sacroiliac joint fusion system, available online at www.zygatech.com.
Donner, E.J., Sacroiliac joint fusion system, U.S. Appl. No. 61/335,947, filed Jan. 13, 2010.

\* cited by examiner

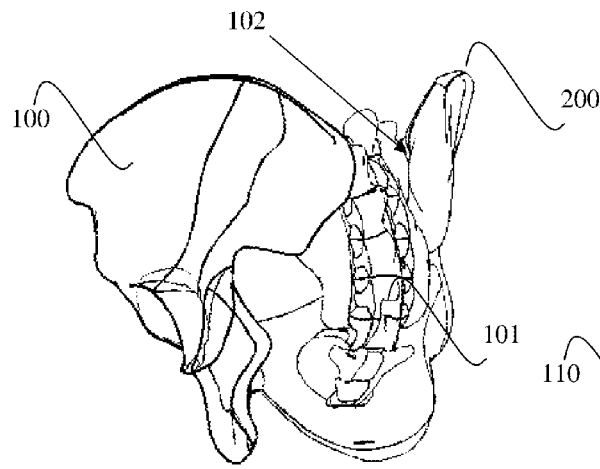
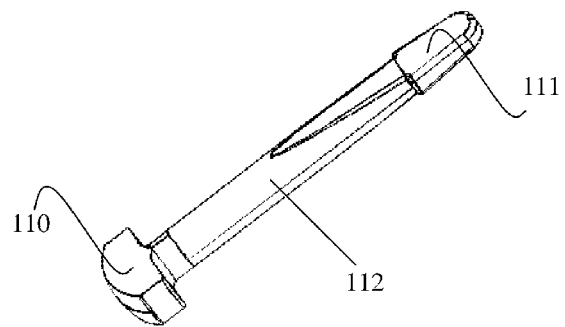
FIG. 7　　　　　　　　FIG. 8
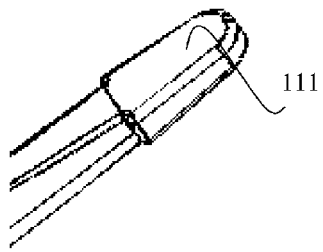
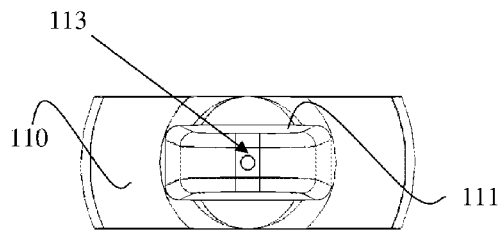
FIG. 9　　　　　　　　FIG. 10
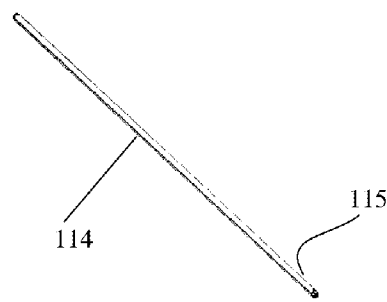
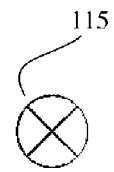
FIG. 11　　　　　　　　FIG. 12

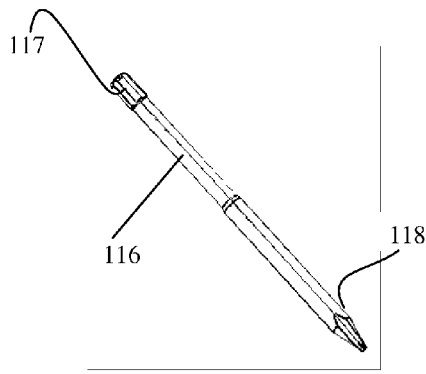
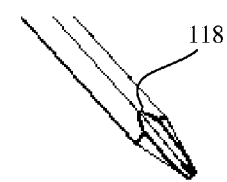
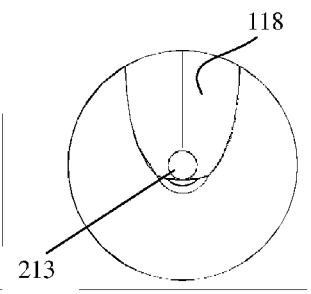
FIG. 13   FIG. 14   FIG. 15
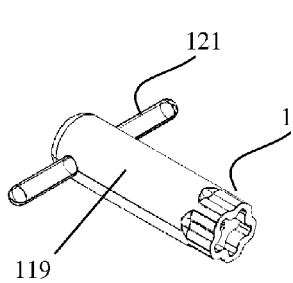
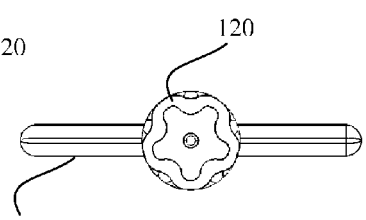
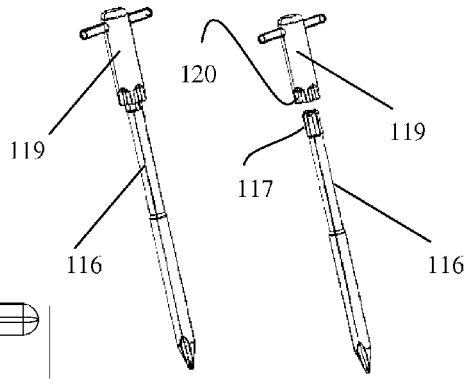
FIG. 16   FIG. 17   FIG. 18   FIG. 19
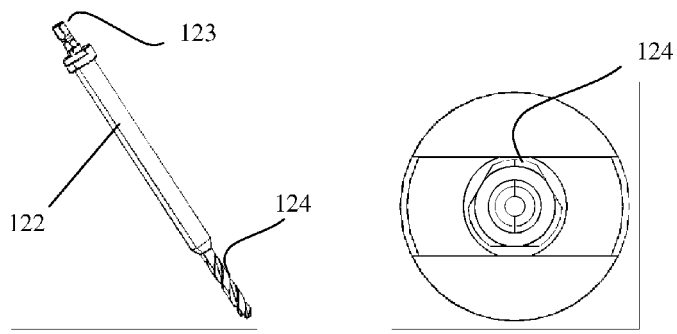
FIG. 20   FIG. 21

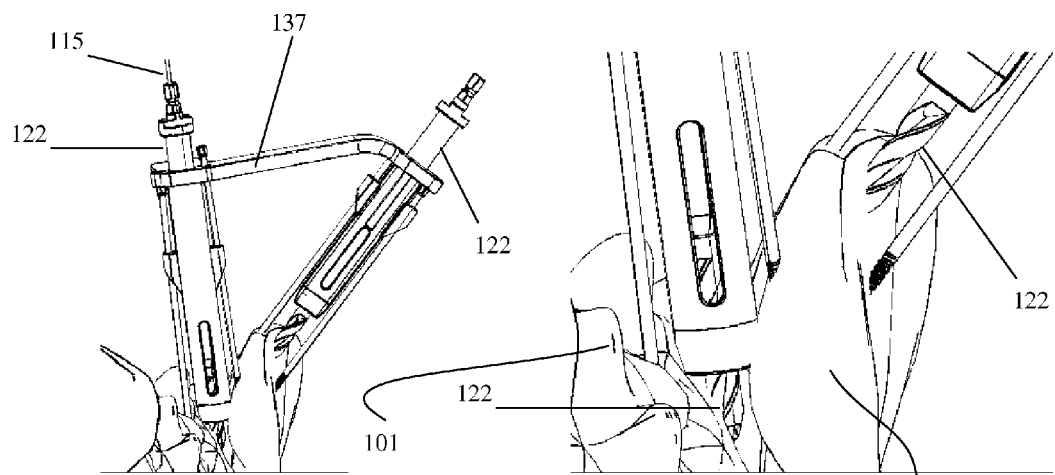
FIG. 59
FIG. 60
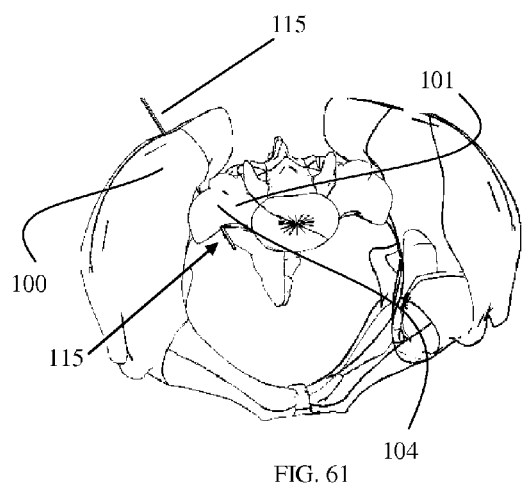
FIG. 61

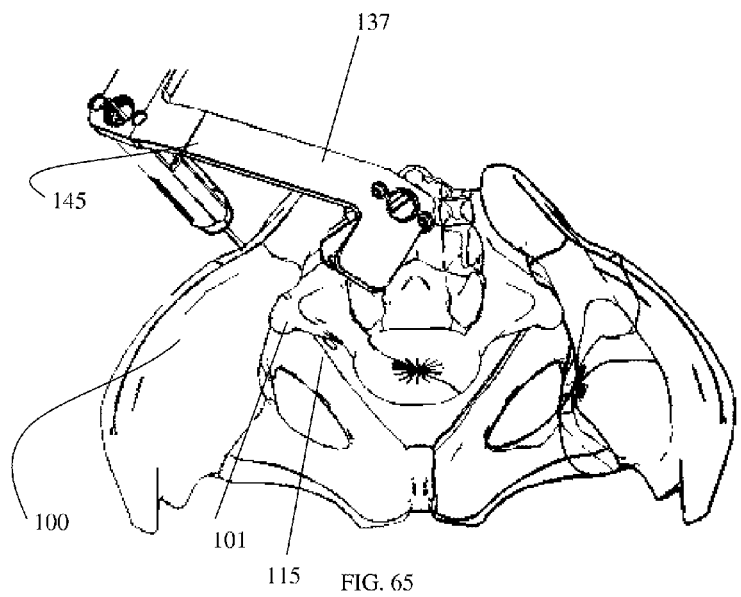
FIG. 65
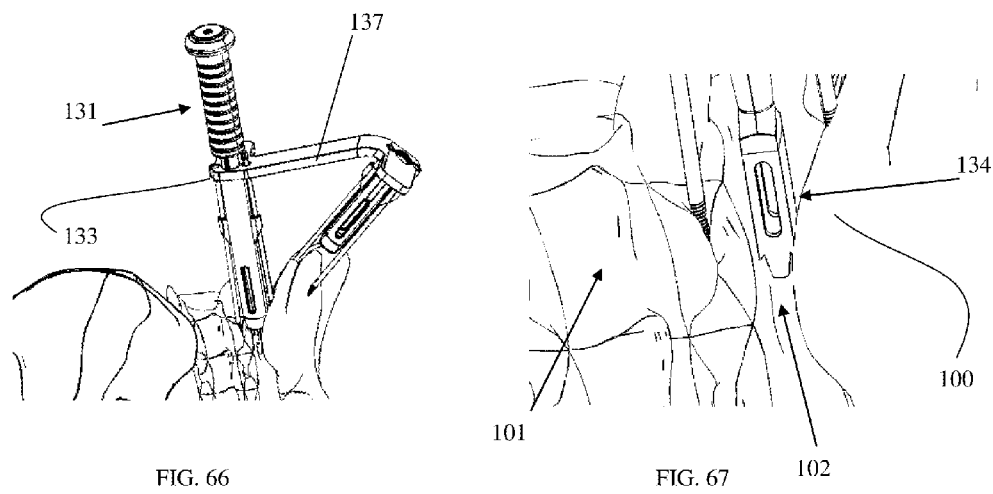
FIG. 66
FIG. 67

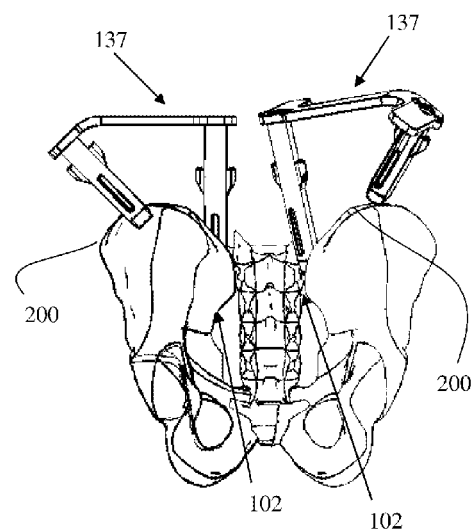
FIG. 82
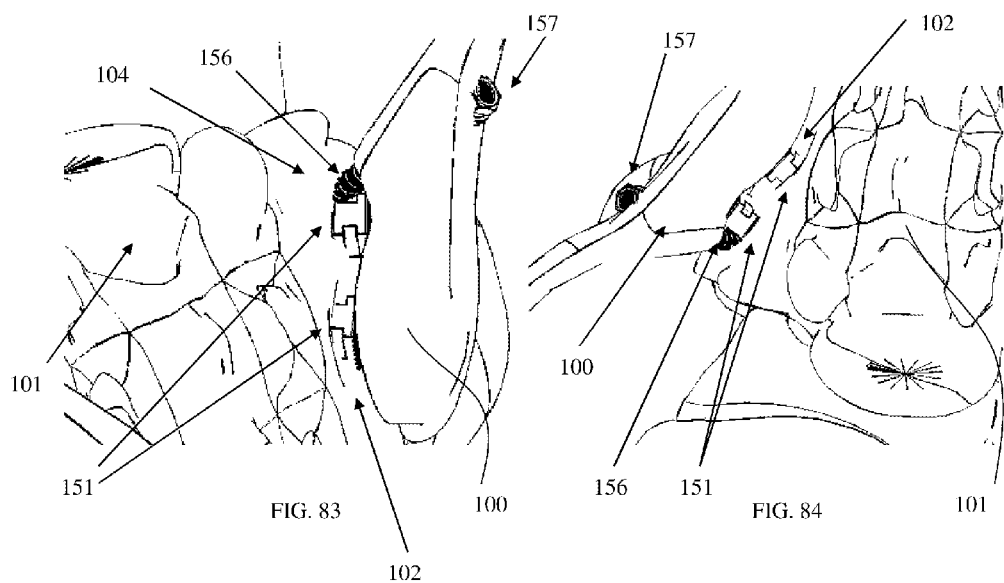
FIG. 83
FIG. 84

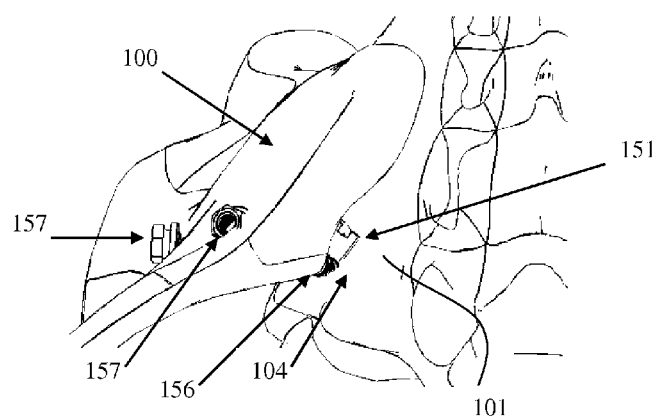
FIG. 85
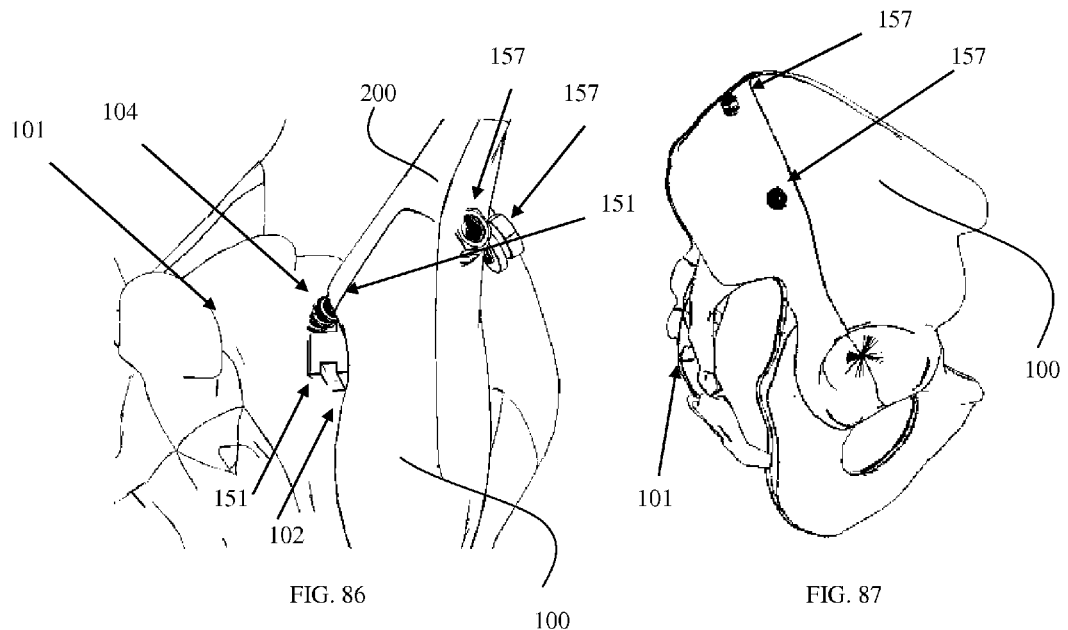
FIG. 86
FIG. 87

METHOD AND IMPLANT SYSTEM FOR SACROILIAC JOINT FIXATION AND FUSION

FIELD OF THE INVENTION

The present invention relates generally to medical devices and medical methods. More particularly, the present invention relates to musculoskeletal surgical methods and associated surgical tools for treatment of the sacroiliac joint.

DISCUSSION OF THE BACKGROUND

Lower back pain is a common ailment among the population and results in both pain and suffering as well as loss of work time. Thus, approaches for the treatment of back pain can both relieve suffering as well as reduce employee down time. Thus, effective treatments for lower back pain have both economic benefits as well as the benefit of alleviating considerable suffering.

The sacroiliac joint is located at the juncture of the ilium, the upper bone of the pelvis, and the sacrum at the base of the spine. While the sacroiliac joint has a limited range of motion, dysfunction of the joint has been identified. The joint is supported by a range of ligaments including, for example, the sacroiliac ligament at the base of the joint and the anterior sacroiliac ligament at the top of the joint.

The sacroiliac joint (SI joint) is increasingly being diagnosed as a common pain generator. That is, SI joint degenerative disease and instability are being diagnosed and treated more commonly. Contributing factors include post traumatic injury, accelerated wear/instability after lumbar fusion, post pregnancy pain/instability and longer life span combined with a more active lifestyle in many patients. In addition, complex spine surgeries, such as for correction of sagittal plane deformity, often require iliac fixation to maintain correction in patients with a high pelvic incidence or high risk of lumbo-sacral hardware failure.

High energy pelvic ring injuries that involve disruption of the SI joint and/or displaced fractures of the sacrum present unique challenges to the orthopedic traumatologist. Some sacral fractures require solid posterior stabilization, which may be difficult to achieve with typical treatment methods. Furthermore, vertically unstable sacral fractures/SI joint disruptions have a relatively high incidence of neurovascular injury and may require unique stabilization. Typically, a spinal surgeon will be involved to perform lumbo-pelvic stabilization of these injuries to provide vertical stability of the injury. However, there may be significant soft tissue trauma associated with these injuries, making extensive surgical approaches of elevated risk in terms of infection and wound complications.

Current techniques and instrumentation systems may require extensive surgical exposure and dissection. Moreover, such instrumentation systems are typically designed for other applications, and not to connect and stabilize the lumbar spine and pelvis. As a result, this can make the surgical times longer and more frustrating for surgeons and surgical staff. For example, traditional posterior iliac screws are often prominent because the posterior iliac crest is relatively subcutaneous. Yet, this sometimes makes hardware painful for the patient and at risk for pressure soreness following surgery.

Furthermore, the current techniques and instruments do not allow for a secure and consistent fusion construct. They provide one or the other many times, but no current system resolves both issues. This may lead to further SI joint instability and a failed surgery.

It is therefore desirable to provide new surgical methods and tools for treating damaged sacroiliac joints that securely and consistently fuse the joint.

SUMMARY OF THE INVENTION

The present invention is an improved methods and devices for the immobilization or fusion of the Sacroiliac joint and apparatuses for facilitating the procedure. Immobilization may refer to mechanical holding or surgical fusion.

It is therefore a primary object of the present invention to provide an improved, combined approach for both mechanical holding and surgical fusion through a novel exposure device is described herein. Specifically, with respect to some embodiments, an approach is described to address the SI joint through a posterior approach while delivering both a fusion device in the form of a bone graft material and a separate fixation device which can be in the form of a screw, or the like. Furthermore, the fusion device is delivered to the joint, placed between the sacrum and ilium, while the fixation device is delivered through the iliac wing, closest to the iliac crest, into the sacrum while not entering or going across the SI joint.

In some embodiments, the present invention relates to a method including creating an incision proximal to the patient's SI joint, creating an incision over iliac wing, dilating the incisions, engaging the exposure device with both incisions, creating a void in the SI joint, inserting a graft into the void, drilling a hole through the ilium and the S1 vertebra of the sacrum, and inserting a joint fusing device in the ilium and sacrum.

In some embodiments, the present invention relates to a method including preparing the patient for surgery (e.g., positioning the patient in a prone position to provide the surgeon access to the SI joint, general or local anesthesia, and the like), making a small incision over the top of the iliac wing from a posterior approach, locating the SI joint and an incision point for access to the SI joint (e.g., by blunt finger palpitation), insertion of a pin or wire to create an incision, insertion of a dilator over the pin and impacting the dilator to dilate the incision to a width through which instruments may be passed, inserting a first working channel of a double-barreled, double-angled exposure device over the dilator and inserting a second working channel of said exposure device in the incision over the iliac wing, securing the first and second working channels in position with fixing pins, removing the dilator, inserting a drill bit apparatus through each of the first and second work channels, using the drill bit apparatus in the first working channel to displace bone in the SI joint thereby creating a void, using the drill bit apparatus (or a second drill bit apparatus) in the second working channel to drill a hole in the iliac crest and the S1 vertebra of the sacrum, removing the drill bit apparatus, loading a graft onto an inserter and inserting the graft and inserter into the first working channel until the graft is positioned proximal to the void in the patient's SI joint, inserting an impactor into the first working channel and applying force to displace the graft into the void in the patient's SI joint, inserting a joint fusion device coupled to a fusion device inserter into the second working channel and implanting said joint fusion device in the hole in the iliac crest and the sacrum, removing all instruments, and closing the incisions.

Additional objects of the invention will be apparent from the detailed descriptions and the claims herein.

BRIEF DESCRIPTION OF THE DRAWINGS

FIG. 7 is an oblique view of the right sacroiliac joint.

FIG. 8 is a perspective view of a joint probe.

FIG. 9 is an enlarged view of the joint probe in FIG. 8.

FIG. 10 is an end view of the joint probe in FIG. 8.

FIG. 11 is a perspective view of a guide pin.

FIG. 12 is an end view of the guide pin in FIG. 11.

FIG. 13 is a perspective view of a joint cutting instrument.

FIG. 14 is an enlarged view of the joint cutting instrument in FIG. 13.

FIG. 15 is an end view of the joint cutting instrument in FIG. 13.

FIG. 16 is a perspective view of a t-handle addition for a joint cutting instrument.

FIG. 17 is an end view of the t-handle addition in FIG. 16.

FIG. 18 is a perspective view of a joint cutting assembly.

FIG. 19 is an exploded, perspective view of the joint cutting assembly in FIG. 18.

FIG. 20 is a perspective view of a drill bit.

FIG. 21 is an end view of the drill bit in FIG. 20.

FIG. 59 is an oblique view of a surgical tool according to an embodiment of the present invention inserted into an SI joint with drill bits present in working channels of the surgical tool.

FIG. 60 is an enlarged oblique view of a surgical tool according to an embodiment of the present invention inserted into an SI joint with drill bits present in working channels of the surgical tool.

FIG. 61 is a superior view of implant placements according to an embodiment of the present invention.

FIG. 65 is a superior view of a surgical tool according to an embodiment of the present invention inserted into an SI joint with the guide pins marking implant placements.

FIG. 66 is an oblique view of a surgical tool according to an embodiment of the present invention inserted into an SI joint with a box chisel inserted into a working channel of the surgical tool.

FIG. 67 is an enlarged oblique view of a box chisel inserted into an SI joint, with a working channel removed from view for clarity.

FIG. 82 is a posterior view of a pelvis with two surgical tools according to an embodiment of the present invention with a bilateral placement of the two surgical tools for the placement of bilateral implants.

FIG. 83 is an enlarged posterior view showing two fusion devices inserted in an SI joint and one fixation device in the ilium.

FIG. 84 is a superior view showing two fusion devices inserted in an SI joint and one fixation device in the ilium.

FIG. 85 is a superior view showing two fixation devices in an ilium and sacrum and one fusion device in an SI joint according to an embodiment of the present invention.

FIG. 86 is an oblique, posterior view showing two fixation devices in an ilium and sacrum and one fusion device in an SI joint according to an embodiment of the present invention.

FIG. 87 is a right, lateral view showing two fixation devices in an ilium and sacrum according to an embodiment of the present invention.

DETAILED DESCRIPTION

Figure 1:
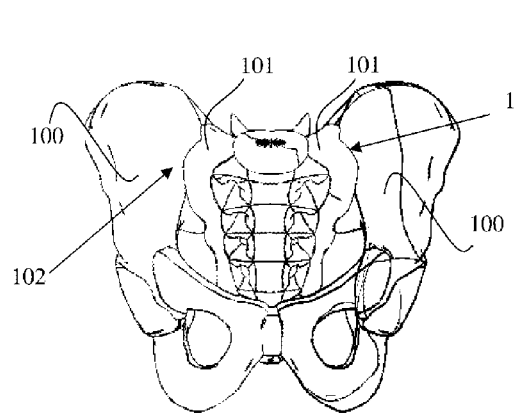
FIG. 1 is an anterior view of the bony anatomy of the pelvis and sacrum.

Reference will now be made in detail to certain embodiments of the invention, examples of which are illustrated in the accompanying drawings. While the invention will be described in reference to these figures and certain implementations and examples of the embodiments, it will be understood that such implementations and examples are not intended to limit the invention. To the contrary, the invention is intended to cover alternatives, modifications, and equivalents that are included within the spirit and scope of the invention as defined by the claims. In the following disclosure, specific details are given to provide a thorough understanding of the invention. References to various features of the "present invention" throughout this document do not mean that all claimed embodiments or methods must include the referenced features. It will be apparent to one skilled in the art that the present invention may be practiced without these specific details or features.

Reference will be made to the exemplary illustrations in the accompanying drawings, and like reference characters may be used to designate like or corresponding parts throughout the several views of the drawings.

The present invention relates to novel surgical tools designed for repairing a damaged or injured sacroiliac joint in a human patient, and methods for using such tools in procedures for repairing the damaged or injured sacroiliac joint. More specifically, the present invention pertains to a method for both a secure fixation element(s) that provides for mechanical stability and a bone fusion element(s) that creates a contiguous piece of bone from the sacrum to the ilium. Both implants may be applied to the SI joint through a novel surgical tool (e.g., an exposure device) without the need for additional patient positioning or secondary surgery.

With respect to some embodiments, an approach is described to address the SI joint through a posterior approach while delivering both a fusion device in the form of a bone graft material and a separate fixation device which can be in the form of a screw, or the like. Furthermore, the fusion device is delivered to the joint, placed between the sacrum and ilium, while the fixation device is delivered through the iliac wing, closest to the iliac crest, into the sacrum while not entering or going across the SI joint.

An exemplary exposure device may include two working channels for guiding various surgical tools during a minimally invasive SI joint repair procedure. The surgical tool may allow the insertion of a graft into the SI joint through one working channel guide in the surgical tool and the insertion of a screw into the ilium and sacrum through a second working channel to mechanically secure the SI joint during the same procedure. The tool enables a minimally invasive surgical method for repairing an SI joint that results in a secure, consistent, and reliable fusion of the SI joint. The surgical tool may also enable the insertion of one or more grafts into the SI joint while avoiding damage to the soft and connective tissues in and around the SI joint due to a round geometry of the working channel guide (a component of the surgical tool) that is inserted into the SI joint. The surgical tool also enables the insertion of a screw or other stabilizing device into the ilium and sacrum such that screw does not traverse the SI joint, thereby further avoiding damage to connective tissue of the SI joint.

Relevant Anatomy Description

Figure 2:
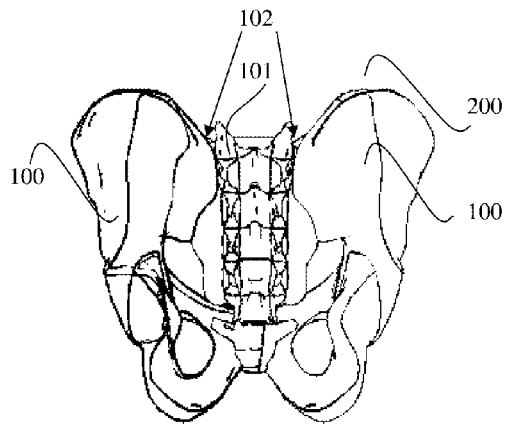
FIG. 2 is a posterior view of the bony anatomy of the pelvis and sacrum.
Figure 3:
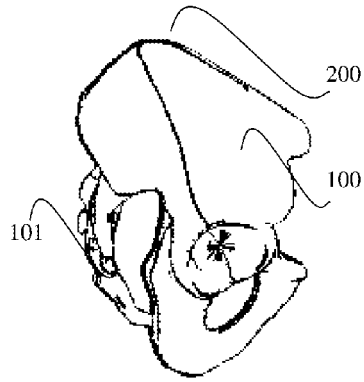
FIG. 3 is a right lateral view of the bony anatomy of the pelvis and sacrum.
Figure 4:
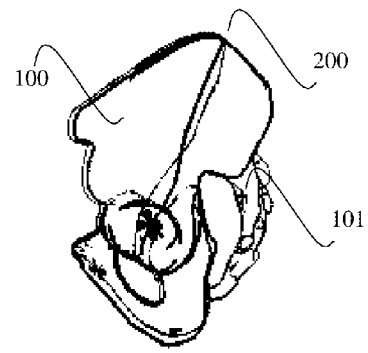
FIG. 4 is a left lateral view of the bony anatomy of the pelvis and sacrum.
Figure 5:
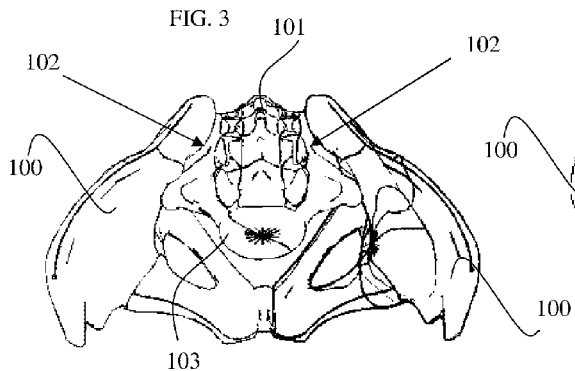
FIG. 5 is a superior view of the bony anatomy of the pelvis and sacrum.

Referring to the drawings, FIG. 1 displays the bony anatomy of the sacrum and pelvis in a frontal, or anterior, view. The SI joint 102 is located between the ilium, or iliac wing, 100 and the sacrum 101 at the base of the pelvis 201. Additionally, the ridgeline of the articular process, the lateral ala and the pedicle of vertebrae 51 can be observed in this view. In FIG. 2., it can be seen that the SI joint 102 is not fully exposed for direct visualization from a rear, or posterior, viewpoint due to the angled and raised iliac crest 200 of the iliac wing 100. This angle provides a landmark for the entry point of the present invention at the posterior iliac crest. In FIG. 3 and FIG. 4., the prominence of the iliac crest 200 is displayed, along with the large surface area of the iliac wing 100, while the SI joint is fully enclosed between the iliac wing 100 and the sacrum 101 and occluded for direct visualization by the iliac wing 100. Again, the landmark of the posterior iliac crest can be seen. From a top down view, or superior view, the sacroiliac joint 102 can be fully observed between the iliac wing 100 and the sacrum 101, as shown in FIG. 5. Also shown in FIG. 5., the full sacrum 101 and specifically the vertebral body of S1. The posterior superior iliac crest and the entry point of the S1 pedicle 104 can be observed in a direct line from one another (see also FIGS. 83-89).

Figure 6:
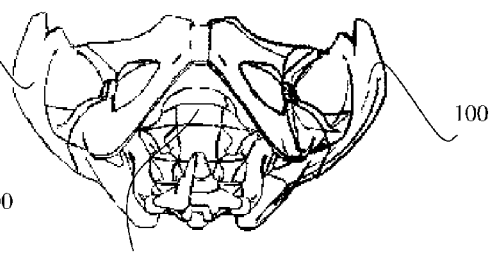
FIG. 6 is an inferior view of the bony anatomy of the pelvis and sacrum.
Figure 22:
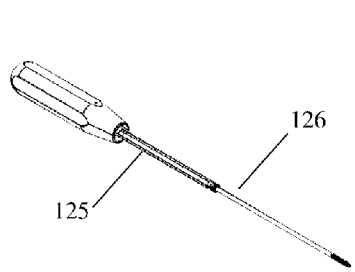
FIG. 22 is a perspective view of a fixation pin insertion assembly.
Figure 23:
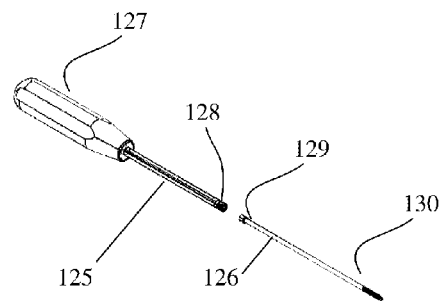
FIG. 23 is an exploded, perspective view of the fixation pin insertion assembly in FIG. 22.

In FIG. 6., it can be again observed that the SI joint is occluded from direct visualization due to the anatomy of the sacrum 101, the ilium 100 and the pelvis. Therefore, the only direct visualization of the SI joint can be achieved through an anterior, superior or posterior-oblique view of the sacrum and pelvis. Due to major organs being present in the pelvic-sacral cavity (colon, rectum, bladder, etc.), an anterior or superior approach to the bony anatomy and, specifically the SI joint, are unreasonable in risk. Lateral approaches can be performed as described in Published U.S. Pat. No. 5,334,205 to Cain, entitled "Sacroiliac Joint Fixation Guide," incorporated herein by reference and Published U.S. Pat. No. 8,221,428 to Trieu, entitled "Sacro-iliac joint implant system, method and instrument," incorporated herein by reference. However, these techniques rely on non-direct confirmation methods such as navigation and fluoroscopy to determine accurate landmark and sacroiliac joint locations. The present invention provides for a surgical technique and novel instrument design which allows for a direct visualization of the SI joint by utilizing a posterior-oblique access method to the anatomy as displayed in FIG. 7. In this drawing, the SI joint 102 can be clearly viewed between the right ilium 100 and sacrum 101. A corresponding joint can be exposed through the same approach on the left hand side. Additionally, the anatomical landmark of the right posterior iliac crest and the corresponding access to the S1 pedicle 104 can be seen through this approach.

Instruments

In some embodiments, the present invention may be a novel surgical tool or a tool kit that may be used in a surgical method for treating a patient's SI joint. Exemplary tools are described herein.

In one embodiment, the surgical tool may be a surgical guiding tool having two working channels therein for guiding other surgical tools for use in repairing an SI joint. The two working channels may be attached to one another by a connecting member, such as a bar or a rack. The bar may have a bend or angle therein that positions the two working channels at an angle (with respect to their longitudinal axes) relative to one another in a range of 0° to 180°. In some embodiments, the angle between the two working channels may be acute (e.g., about 30° to about 50°, or any angle in that range, such as about 45°). The angled positions of the two working channels allows one working channel to be positioned over the SI joint and the second working channel to be positioned over the ilium (e.g., the iliac wing) simultaneously and snugly, enabling the insertion of one more grafts into the SI joint and a joint fusion device (e.g., a bone screw) into the ilium and sacrum in a single procedure with a simple tool, without the need to reposition the surgical tool to insert either the graft or the joint fusion device. In further embodiments, the relative angle of orientation of the two working channels may be a right angle or may be obtuse, depending on the desired insertion point on the ilium. If a different entry point for a joint fusion device is desired, the relative orientation angle of the two working channels may be in a range of about 45° to about 180° (e.g., about 90° to about 180°, about 45° to about 135°, about 90° to about 120°, or any value or range of values therein). For example, if the desired entry point on the ilium is more lateral or anterior, the angle of orientation between the two working channels may be 90° or greater.

Referring to FIGS. 27-31, a double-barreled, double-angled surgical tool 137 is shown have a connecting bar 137 connecting a first working channel 239 and a second working channel 240. The connecting bar 137 may have a bend or angle 143 between the first and second working channels 239 and 240. The bend 143 may have an obtuse angle in a range of about 110° to about 160° (e.g., about 135° or any value therein). The bend 143 results in the first and second working channels being positioned at an acute angle relative to one another that is complementary to the obtuse angle of the bend 143. In alternative implementations, the connecting bar may have a lockable joint therein between the first and second working channels 239 and 240 that may be adjusted to have an angle in a of about 90° to about 180° (e.g., about 135° or any value therein). The angle of the connecting bar 143 is configured to accommodate the contour of the pelvis between the ilium and the SI joint such that the first working channel 239 can be engaged with a posterior side of the sacroiliac joint and the second working channel 240 can be engaged with a posterior portion of the ilium simultaneously.

Figure 29:
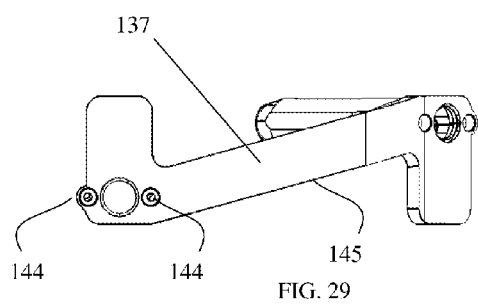
FIG. 29 is a top view of a surgical tool according to an embodiment of the present invention.
Figure 30:
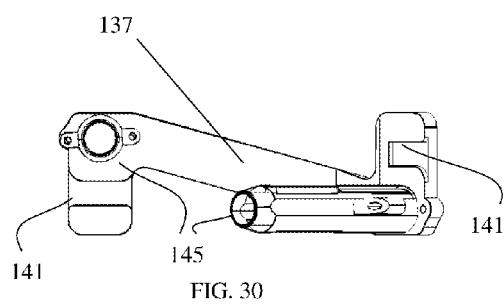
FIG. 30 is a bottom view of a surgical tool according to an embodiment of the present invention.

The connecting bar 137 may also have a second angle therein, as shown in the top perspective of FIG. 29 and the bottom per. The first and second working channels 239 and 240 may be position at an angle between about 5° and about 40° (e.g., about 15°, or any angle therein). To further illustrate, the bar 143 may be angled such that the longitudinal axes of the first and second working channels 239 and 240 may run along different, but parallel planes. Thus, the working channels 239 and 240 are positioned at an acute angle relative to one another from a side perspective (e.g., FIG. 28), and on parallel planes relative to each other from top or bottom perspective (e.g., FIGS. 29 and 30). The additional angle in the connecting bar 143 may aid in positioning the second working channel 240 on the ilium when the first working channel is engaged with the SI joint, such that the second working channel 240 is positioned over the iliac wing, close to the iliac crest. The position and angle of the second working channel 240 may allow the insertion of a bone fusion device (e.g., a bone screw) through the ilium and the sacrum (e.g., the S1 vertebrae) through the hollow barrel of the second working channel 240, such that the bone fusion device does not traverse the SI joint (e.g., it is inserted anteriorly to the SI joint).

Each working channel have a hollow barrel therein for passing various surgical tools that have a shape corresponding to (complementary to) the hollow barrel. The working channels provide a guide for inserting the various surgical tools into the SI joint and the ilium, allowing precise surgical incisions, insertions of grafts, etc. Each of the first and second working channels 239 and 240 may have one or more pin guide slots 139 on a side thereof for insertion of fixing pins to immobilize the surgical tool 137 when it is engaged with the SI joint and the ilium.

The first and second working channels may each have one or more windows 138 in sides of the hollow barrels allowing the progress of a tool inserted therein to be observed through the one or more windows. For example, a surgical implement (e.g., a dilator) inserted into the hollow barrel of working channel 239 may have notches or unit markings on a side thereof that are visible through the one or more windows 138, allowing the progress and depth of the surgical implement to be precisely known. The windows 138 may also allow access to the surgical implements inserted into the first and second working channels. If a surgical implement becomes difficult to remove during a surgical procedure due to the presence of fluid in the hollow barrel of the working channel (e.g., creating suction), appropriate tools can be used to access the surgical instrument through the windows 138 to aid in the removal of the surgical implement.

Figure 31:
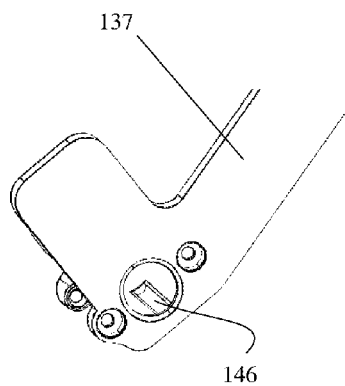
FIG. 31 is an isolated, top view of a surgical tool according to an embodiment of the present invention.

Referring to FIG. 31, the hollow barrels of the first and second working channels 239 and 240 may have a slot 146 (e.g., a timing feature) that arrests the progress of a surgical implement inserted into the hollow barrel of the channel. The slot 146 prevents the surgical implement from advance too far into the SI joint or the ilium and sacrum, thereby preventing damage to the tissue of the patient. The surgical implements used in connection with the double-barreled, double-angled surgical tool may have a protrusion that is complementary to the slot 146, such that the slot is effective in controlling a depth to which the surgical implement can be inserted. The slot 146 also ensures that such surgical implements having a complementary protrusion are and remain properly oriented in the hollow barrel of the working channel, with no axial movement, during the surgical procedure.

The insertable end 142 of the first working channel 239 may have a round or circular geometry that prevents or reduces damage to the soft and connective tissues in and around the posterior side of the SI joint. Guide channels having other shapes (e.g., rectangular or square) may damage soft tissues around the SI joint when the guide channels are inserted therein. The round geometry of the insertable end 142 favorably reduces or prevents such damage. The round or circular insertable end 142 may also have a tapered or rounded profile, which may further aid in reducing or preventing damage to the soft and connective tissues around the SI joint. The second working channel 240 may also have circular and/or rounded or tapered insertable end 142, as well. It is to be appreciated that the present invention is not limited to working channels having round, circular, or rounded ends. The working channels may have other perimeter shapes circular, oval, triangular, polygonal (pentagonal, hexagonal, etc.), Reuleaux shapes, and other applicable shapes.

The first and second working channels may have other additional features such as handles 140 and slots 141 therein (e.g., for inserting handle extensions), as well. It is to be appreciated that the above description of the surgical tool does not limit the present invention, and other features are contemplated in the present invention.

In some embodiments the invention may comprise one or more separate working channels that may be used in a similar manner to the double-barreled, double-angled exposure device. In reference to FIG. 77, the invention may include first and second working channels 290, which can be individually positioned, for example, with one inserted into the posterior of the SI joint, and another positioned over the iliac wing. In such embodiments, the individual working channels may have the same features described above with respect to the double-barreled, double-angled exposure device, except for the connecting bar 143 and the features particular thereto.

In some embodiments, the invention may include two separate working channels that may be used in a similar manner to the double-barreled, double-angled exposure device, and that may be positioned individually, and then secured by an adjustable rack in order to stabilize the working channels during a surgical procedure. In reference to FIG. 78, first and second working channels 290 may be first individually positioned (e.g., with one inserted into the posterior of the SI joint, and the other positioned over the iliac wing), and attached to rack 161. In such embodiments, the individual working channels may have the same features described above with respect to the double-barreled, double-angled exposure device, except for the connecting bar 143 and the features particular thereto. Also, in such embodiments, the handle 140 of the individual working channels may have a slot, a latch, or some other fastening device thereon for receiving and securing the rack 161. Additionally, the handle 140 may also be attachable to a stabilizing structure (e.g., a table or surgical arm, etc.) to prevent movement of the exposure device or surgical implements engaged therewith during surgical procedure.

In some embodiments the invention may comprise a double-barreled working channel having side by side (e.g., parallel) hollow barrels, each able to receive and guide surgical implements. The two barrels may be have a same or different length. In reference to FIGS. 80-81, a double-barreled working channel 295 may have first and second parallel barrels. Working channel 295 may allow multiple bone grafts to be inserted into an SI joint. Such embodiments may include an additional second working channel having a single hollow barrel, which may or may not be attachable to the double-barreled working channel with a adjustable rack. In such embodiments, the double-barreled working channel may have similar features as described above with respect to the working channels double-barreled, double-angled exposure device, except for the connecting bar 143 and the features particular thereto.

In some embodiments, the invention may include a kit or set of surgical implements that are associated with one or more of the exposure devices described above. Various tools may be included in such a set, including a joint cutting instrument (e.g., dilator), guide pins, guide pine assemblies, a drill, drill bits, a rasp, a box chisel, an inserter, and an impactor. Each of such tools may correspond to the exposure devices described herein. For example, the joint cutting instrument, the drill bits, the rasp, the box chisel, the inserter, and the impactor each may have a shape that is complementary to a hollow barrel of the exposure device, allowing each instrument to be inserted into the hollow barrel flushly in the proper orientation, without room to deviate from the path of the barrel. Thus, the working channels of the exposure devices may act as precise guides for the surgical implements described above.

These surgical implementss may be made of any suitable material, including medical grade plastics, metals, or alloys. In some embodiments the tools are single use, in other embodiments the tools may be reused (and autoclaved, cleaned or otherwise suitably disinfected for further use). The tools may have various configurations, including those that differ from those depicted and specifically described herein.

The implements may include a joint probe capable of being used to locate an insertion point in an SI joint for a bone graft. The joint probe may have a hollow channel therethrough for inserting a guide wire into the SI joint once the joint probe is properly positioned in the insertion point. Referring to FIGS. 8-11, the joint probe may have a rounded tip 111 for locating the insertion point, a shaft 112, and a handle 110. A hollow channel 113 run through the length of the joint probe to allow a guide wire to be inserted therethrough and into the SI joint.

The set of tools may also include guide pins for securing the exposure device to the SI joint and the ilium. Referring to FIGS. 11-12, the guide pin 115 may have shaft that corresponds to the central channel of the joint probe and may be inserted into the SI joint through the dilator, to guide tools and implements subsequently positioned in said SI joint.

The set of surgical implements may include a dilator, which may be any device or structure capable of dilating an incision made in a human or other animal. FIGS. 13-19 illustrate an example of a dilator that may be included in the present invention. Dilator 116 may be made of any suitable material and may have any suitable dimensions and configuration. In the depicted example, dilator 116 has a distal end 117, a proximal end 118, and a shaft therebetween. Proximal end 118 may have any configuration suitable to dilate an opening or incision, for example an incision made by a pin or wire, in a human's flesh and dilate that incision to increase its size. The proximal end 118 may be tapered, coming to a point at its end. The distal end 117 may be faceted, allowing it to be engaged with a grooved end 120 of a t-handle 119. A dilator assembly, an example of which is shown in FIGS. 18 and 19, allows the dilator to be spun or otherwise manipulated to adjust the size of an incision. The dilator 116 (and the t-handle 119) may have a central channel running down its length that may allow a guide wire or pin to be inserted therethrough into the incision.

Fixing pins 126 and a fixing pin handle 125 may be included in the set of tools that correspond to the pin guide slots 139 on sides of the working channels of the exposure devices. The guide pins may also have a sharp and/or threaded end 115 for piercing bone and other tissues. The fixing pins may corresponds to the pin guide holes 139 on sides of the working channels of the exposure devices described above. The fixing pins can be used to secure the working channels in a desired position over the SI joint or the ilium.

A drill 122 may be included in the set to allow for bone preparation for implant and graft material insertion. The drill may have a thread portion 124 with numerous designs in order to provide with the desired female thread cut in the desired anatomy. The drill may also be designed to be attached to power instruments, a hand drill or a handle. FIG. 20 displays a drill with a Jacob's chuck connection 123 so that it can be attached to a powered drill for quick preparation. Additionally, the drill may have a central channel 124 running down its length that may allow a guide wire or pin 114 to be inserted there through into the incision as seen in FIG. 21.

Figure 24:
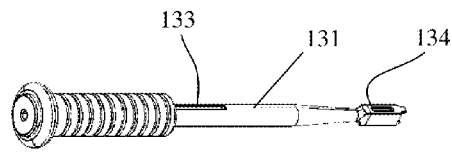
FIG. 24 is a side view of a box chisel.

A chisel 131 may be included in the set to provide an opening in the bone with desired dimensions on its distal tip 134 to better facilitate entry for the implant and bone graft materials. The distal tip 134 may have a tapered nose in order to self-distract its way in between the sacrum and ilium. The distal tip 134 may also have cutting edges to dig into the bone and remove it from the surgical site. The distal tip 134 may also have a containment device for removal of surgical site bone and windows may exist in the containment device to remove said bone after removal from surgical site. The distal tip 134 may be undersized to the implant 151 to ensure full bony contact on all sides of the fusion site. The chisel may have an outer diameter as seen in FIG. 24, that matches the inner diameter of a working channel 290 to keep the chisel directed in an axial plane for desired implant preparation. The chisel may have a timing feature 133 that mates with a female timing feature 146 on the inside of a working channel 290 to keep the chisel from plunging to far into the surgical site and to further keep the chisel in the proper orientation for desired implant site preparation.

Figure 25:
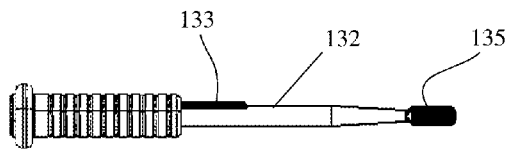
FIG. 25 is a side view of a rasp.

Additionally, a rasp 132 may be included in the set to provide an opening in the bone with desired dimensions on its distal tip 135 to better prepare the bone for a fusion site for the implant. The distal tip 135 may have a tapered nose in order to self-distract its way in between the sacrum and ilium. The distal tip 135 may have aggressive teeth which can scrape the bone to prepare for a non-interrupted interface between the bone graft material from the implant and the host bone of the surgical site. The distal tip 135 may be undersized to the implant 151 to ensure full bony contact on all sides of the fusion site. The rasp may have an outer diameter as seen in FIG. 25, that matches the inner diameter of a working channel 290 to keep the rasp directed in an axial plane for desired implant preparation. The rasp may have a timing feature 133 that mates with a female timing feature 146 on the inside of a working channel 290 to keep the instrument from traveling too far into the surgical site and to further keep the instrument in the proper orientation for desired implant site preparation.

Figure 26:
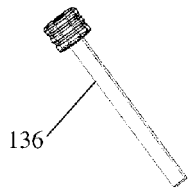
FIG. 26 is a perspective view of a bone graft impactor.
Figure 27:
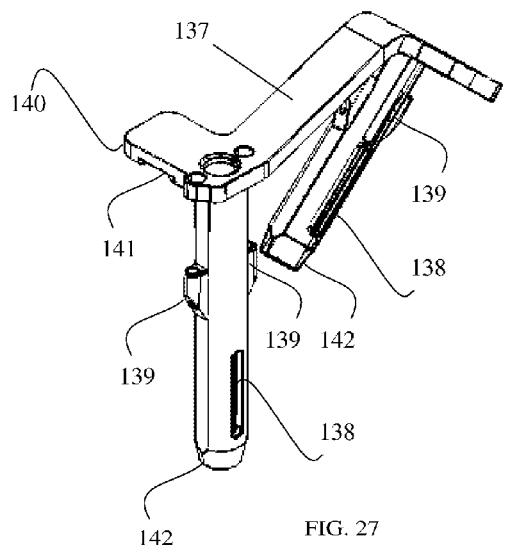
FIG. 27 is a perspective view of a surgical tool according to an embodiment of the present invention.
Figure 28:
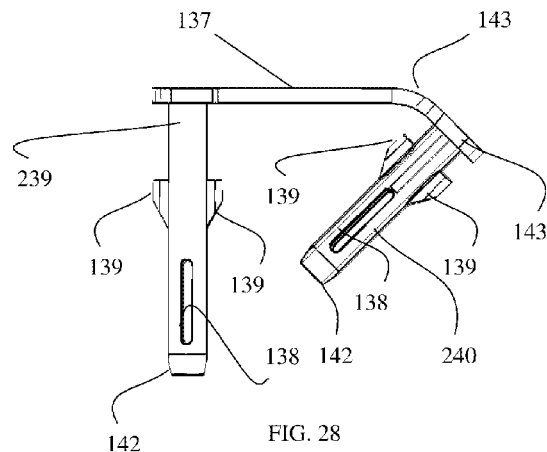
FIG. 28 is a side view of a surgical tool according to an embodiment of the present invention.

One or more impactors, such as impactor 136 shown in FIG. 26, may be included in the surgical implements, as well. The impactor may have a cylindrical proximal end, like a hammer. The impactor may be included in the set to facilitate secondary impaction and movement of the implant 151 and to impact therapeutic bone graft materials such as amniotic stem cells, donor bone or other fusion catalysts in front of and behind the implant to better prepare the surgical site for fusion. The impactor may have an outer diameter, as seen in FIG. 26, that matches the inner diameter of a working channel 290 to keep the instrument directed in an axial plane for desired surgical site preparation.

Figure 32:
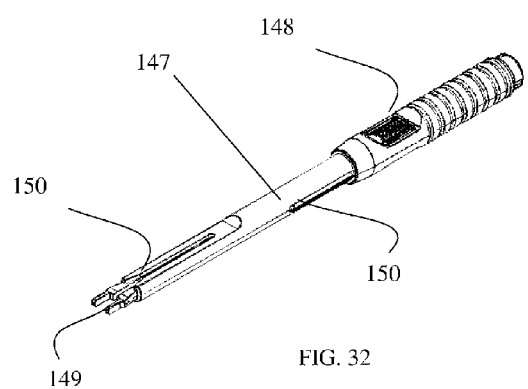
FIG. 32 is a perspective view of a fusion implant or bone graft inserter for use with a surgical tool according to an embodiment of the present invention.

Inserters for fusion devices may be included in the set to facilitate delivery of implants or grafts into the sacroiliac joint and into the ilium and sacrum. A fusion inserter 147 can be used to deliver a bone graft or similar fusion type implant of desired materials such as PEEK, metal or biologic material into the surgical site. As seen in FIG. 32, the inserter may have a thumbwheel 148 that is attached to a spring element 150. When thumbwheel 148 is tightened, spring element 150 is tightened down onto implant 151 to keep the implant from disengaging from the inserter during implantation. Fork arms 149 enter the implant at recesses 152 to keep the implant from losing its desired orientation during insertion. Upon desired placement of the implant, thumbwheel 148 is loosened and the spring element 150 detaches from the implant, leaving the implant in the desired position. The inserter 147 may have an outer diameter as seen in FIG. 32, that matches the inner diameter of a working channel 290 to keep the inserter directed in an axial plane for desired implant preparation. The inserter may have a timing feature 150 that mates with a female timing feature 146 on the inside of a working channel 290 to keep the instrument from traveling too far into the surgical site and to further keep the instrument in the proper orientation for desired implant site preparation.

It is to be appreciated that additional surgical tools or implements may be used with the present working channels, and that the invention is not limited to use of the implements described in this section.

Surgical Methods

In some embodiments, the methods of the present invention substantially fuse the SI joint, such that movement in the joint is minimized or substantially eliminated, thereby diminishing or substantially eliminating the patient's pain and discomfort. More specifically, an improved, combined approach for both mechanical holding and surgical fusion through a novel exposure device is described herein. Specifically, with respect to some embodiments, an approach is described to address the SI joint through a posterior approach while delivering both (1) a fusion device in the form of a bone graft material and (2) a separate fixation device which can be in the form of a screw, or the like. Furthermore, the fusion device is delivered to the joint, placed between the sacrum and ilium, while the fixation device is delivered through the iliac wing, closest to the iliac crest, into the sacrum while not entering or going across the SI joint.

In some embodiments the method involves numerous steps including, creating an incision proximal to the patient's SI joint, creating an incision over iliac wing, dilating the incisions, engaging the exposure device with both incisions, creating a void in the SI joint, inserting a graft into the void, drilling a hole through the ilium and the S1 vertebra of the sacrum, and inserting a joint fusing device in the ilium and sacrum.

Other embodiments include some or all of the following steps, preparing the patient for surgery (e.g., positioning the patient in a prone position to provide the surgeon access to the SI joint, general or local anesthesia, and the like), making a small incision over the top of the iliac wing from a posterior approach, locating the SI joint and an incision point for access to the SI joint (e.g., by blunt finger palpitation), insertion of a pin or wire to create an incision, insertion of a dilator over the pin and impacting the dilator to dilate the incision to a width through which instruments may be passed, inserting a first working channel of a double-barreled, double-angled exposure device over the dilator and inserting a second working channel of said exposure device in the incision over the iliac wing, securing the first and second working channels in position with fixing pins, removing the dilator, inserting a drill bit apparatus through each of the first and second work channels, using the drill bit apparatus in the first working channel to displace bone in the SI joint thereby creating a void, using the drill bit apparatus (or a second drill bit apparatus) in the second working channel to drill a hole in the iliac crest and the S1 vertebra of the sacrum, removing the drill bit apparatus, loading an implant (e.g., a graft) onto an inserter and inserting the implant and inserter into the first working channel until the implant is positioned proximal to the void in the patient's SI joint, inserting an impactor into the first working channel and applying force to displace the implant into the void in the patient's SI joint, inserting a joint fusion device coupled to a fusion device inserter into the second working channel and implanting said joint fusion device in the hole in the iliac crest and the sacrum, removing all instruments, and closing the incisions.

Some embodiments include the use of embodiments of the tools or tool sets of the present invention, as described above. Other embodiments of the methods of the present invention are performed without using the tools of the present invention. The methods of the present invention may be performed in addition to or in conjunction with one or more of the known methods. Embodiments of the methods of the present invention (and tools of the present invention) are now further described with reference to the Figures. Although the methods are described with respect to the use of certain tools, other tools with different structures may be used and still be within the scope of the present invention.

FIGS. 47-74 illustrate a surgical procedure for fusing an SI joint with both a graft inserted in the SI joint and a joint fusion device (e.g., a bone screw). The procedure includes positioning a patient in the prone position and administering either a local or general anesthetic. Blunt finger palpitation may be used to locate the patient's iliac wing and the SI joint. Alternatively, suitable locations for an incision may be determined by imaging methods (e.g., x-ray), or any other suitable method. An incision may then be made over the iliac wing near the iliac crest for the insertion of the second working channel 240 of the double-barreled, double-angled exposure device.

Using a joint probe 112 the insertion area on the posterior side of the SI joint may be determined. The area of the SI joint may be probed until the rounded geometry of the joint probe 112 drops into the proper position in the SI joint, where an incision should be made. Subsequently, a guide pin 114 may be inserted through a central channel in the joint probe and into the patient to create an incision in the SI joint. Alternatively, the incision may be made by any suitable method, including scalpel or other cutting or dissection tool. The incision may be made proximal to the patient's SI joint, allowing the joint to be accessed by the exposure device. The guide pin 114 may be advanced until its proximal end is in contact with the SI joint or at least partially within SI joint.

As shown in FIGS. 51-54, a dilator may be used to dilate the incision. As an example, dilator 116 may be slotted over guide pin 114 through a central channel running the length of the dilator 116. The proximal end of the dilator 116 may be slotted over the guide pin 114, and dilator 116 may then be advanced to or near the SI joint through incision. As dilator 116 enters the incision, the tapered end 118 pushes the patient's flesh and tissue aside, thereby dilating incision to accommodate exposure device. A joint cutting assembly that includes the dilator 116 and a t-handle 120 engaged with a distal end of the dilator 116 may be used to further drive the dilator 116 into the incision to a desired depth to sufficiently expose the SI joint. Alternatively, an impactor (not shown) may be used to further drive the dilator 116 into the incision to a desired depth.

Figure 53:
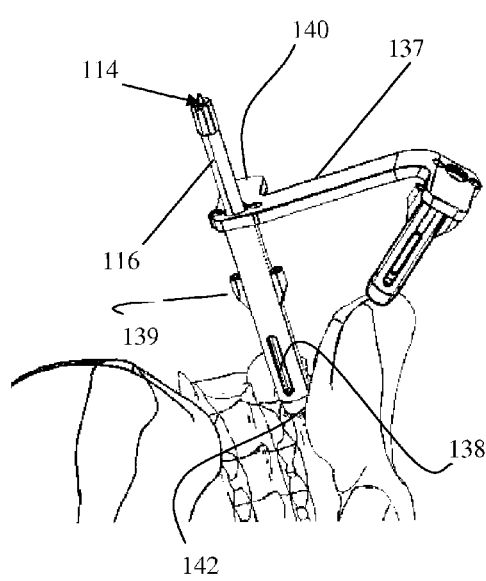
FIG. 53 is an oblique view of a surgical tool according to an embodiment of the present invention inserted into an SI joint.
Figure 54:
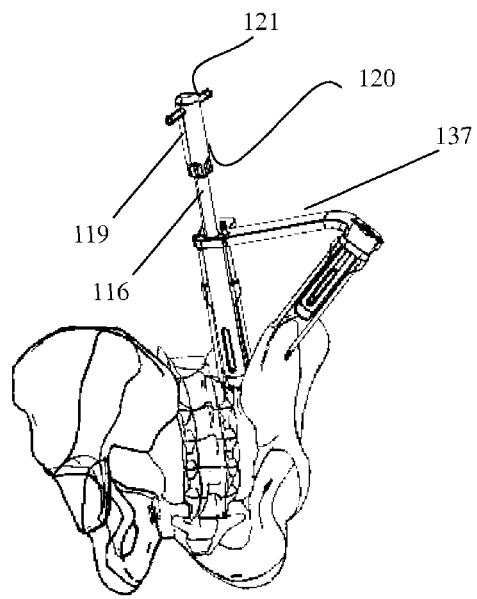
FIG. 54 is an oblique view of a joint cutting assembly and a surgical tool according to an embodiment of the present invention inserted into an SI joint.

FIG. 53 illustrates the placement of the double-barreled, double-angled exposure device over the dilator 116. The exposure device is advanced over dilator 116 and into incision. Dilator 116 enters the hollow barrel of exposure tool at the distal end of the first working channel 239. The first working channel 239 of the exposure tool has proximal end 142 having a round geometry and/or a tapered rounded profile that is operable to distract the SI joint with minimal damage to soft and connective tissue in and around the posterior side of the SI joint. It is to be appreciated that the working channel may have other perimeter shapes circular, oval, triangular, polygonal (pentagonal, hexagonal, etc.), Reuleaux shapes, and other applicable shapes. The exposure device may also further dilate incision. The exposure device is advanced toward SI joint through incision until proximal end 142 is in contact with the SI joint or proximal to the SI joint and in contact with the sacrum and/or ilium. In such embodiments, dilator 116 functions to guide the proximal end 142 to the patient's SI joint.

The exposure device may be configure such that when the first working channel 239 of the exposure device is established in position in or near the SI joint the second working channel 240 is oriented over the iliac wing near the iliac crest (the location of the incision) and in an orientation that will allow the second working channel to guide a drill bit through the ilium and sacrum (e.g., the S1 vertebra) without traversing the SI joint (i.e., without causing damage to the SI joint. The relative position of the first and second working channels of the double-barreled, double-angled exposure device accommodates the contour of the pelvis between the ilium and the SI joint such that said first working channel can be engaged with a posterior side of the SI joint and said second working channel can be engaged with a posterior portion of the iliac wing at an angle that is aligns a longitudinal axis of the second working channel anterior to the SI joint.

Figure 55:
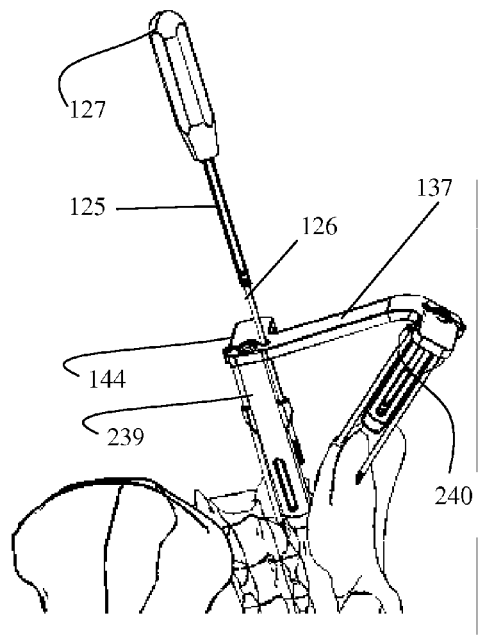
FIG. 55 is an oblique view of an SI joint with a surgical tool according to an embodiment of the present invention and a fixation pin assembly.
Figure 56:
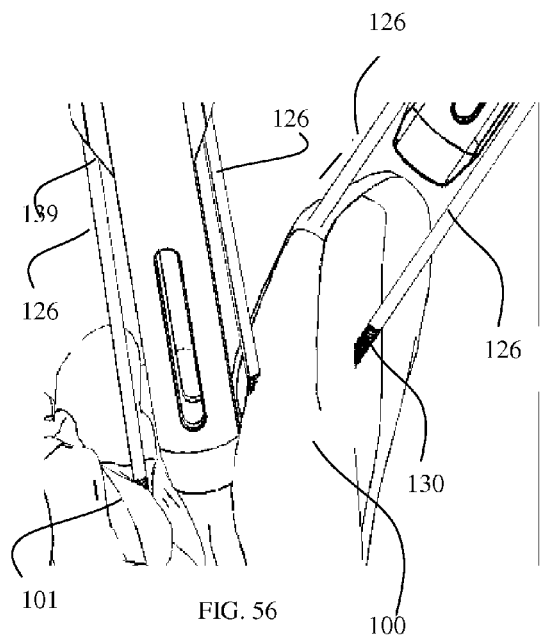
FIG. 56 is an enlarged oblique view displaying a fixation pin assembly and a surgical tool according to an embodiment of the present invention.
Figure 57:
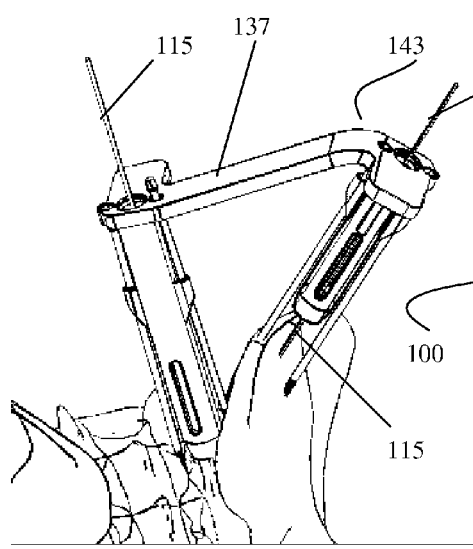
FIG. 57 is an oblique view of a surgical tool according to an embodiment of the present invention inserted into an SI joint with the guide pins marking implant placements.
Figure 58:
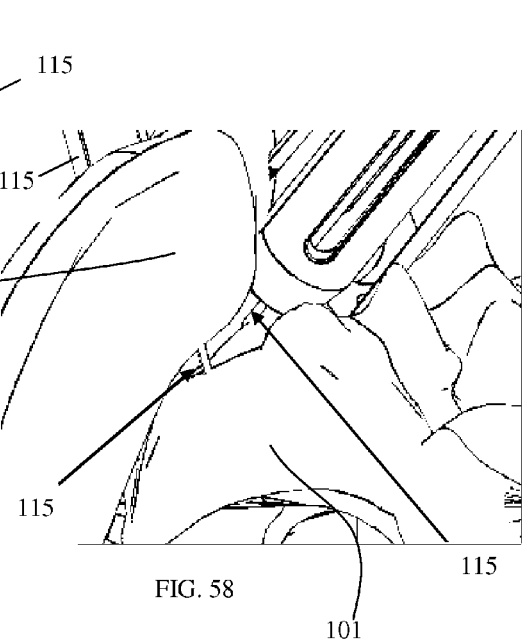
FIG. 58 is an enlarged, superior view of a surgical tool according to an embodiment of the present invention inserted into an SI joint with the guide pins marking implant placements.
Figure 62:
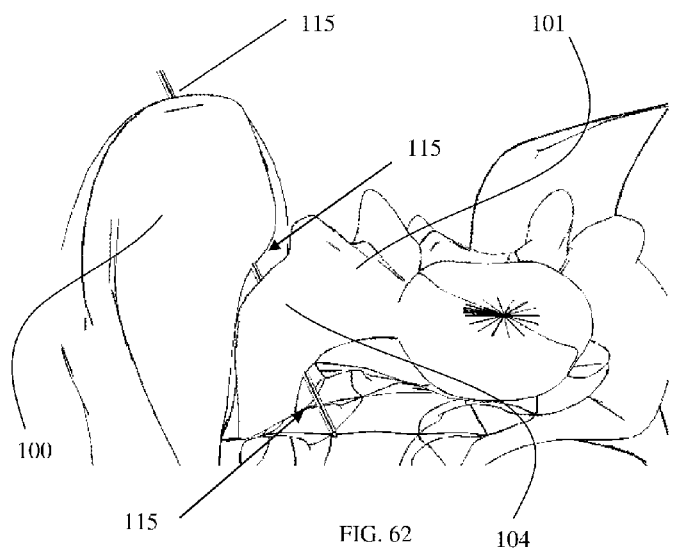
FIG. 62 is an enlarged superior view of implant placements according to an embodiment of the present invention.
Figure 63:
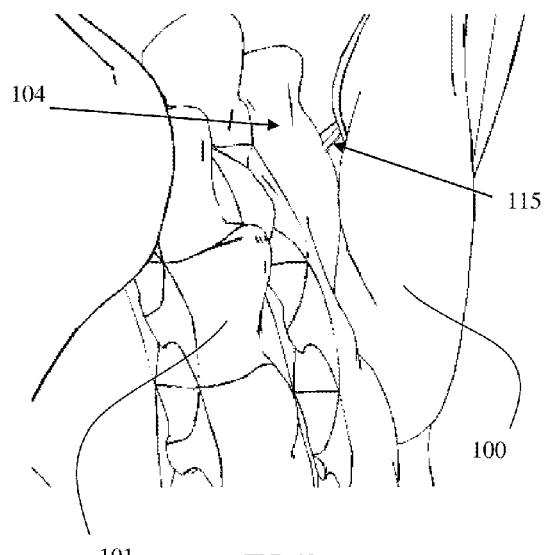
FIG. 63 is an enlarged, posterior view of implant placements according to an embodiment of the present invention.
Figure 64:
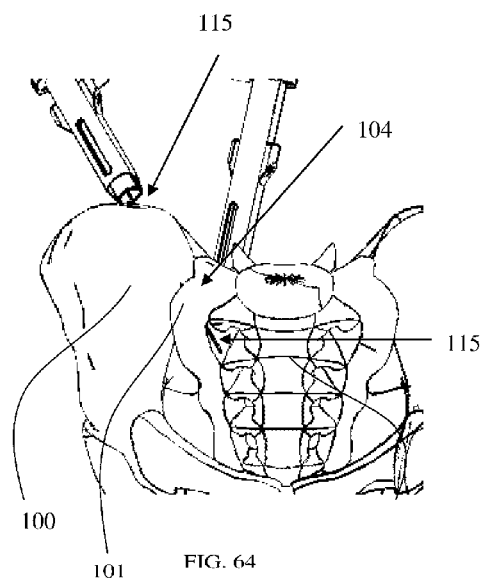
FIG. 64 is an anterior view of a surgical tool according to an embodiment of the present invention inserted into an SI joint with the guide pins marking implant placements.
Figure 68:
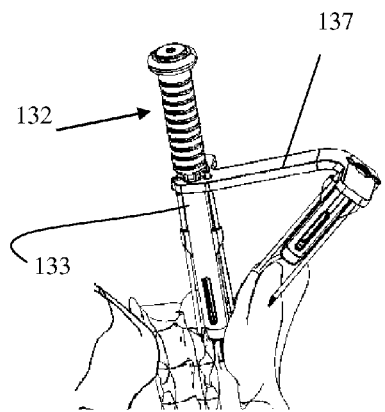
FIG. 68 is an oblique view of a surgical tool according to an embodiment of the present invention inserted into an SI joint with a rasp inserted into a working channel of the surgical tool.
Figure 69:
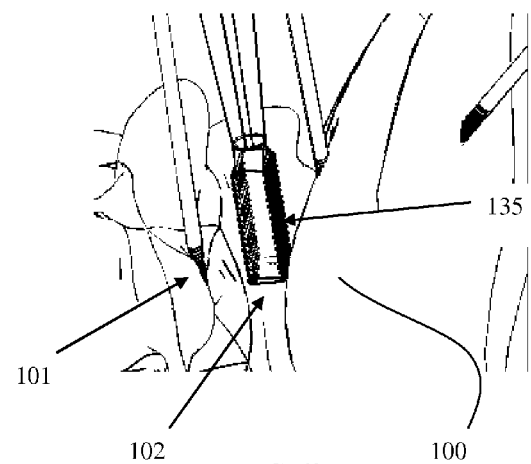
FIG. 69 is an enlarged oblique view of a rasp inserted into an SI joint, with a working channel removed from view for clarity.
Figure 70:
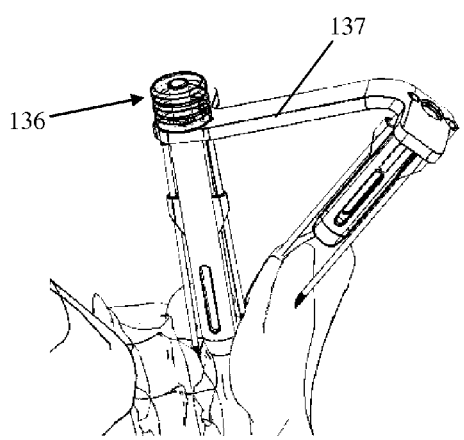
FIG. 70 is an oblique view of a surgical tool according to an embodiment of the present invention inserted into an SI joint with a bone graft impactor inserted into a working channel of the surgical tool.
Figure 71:
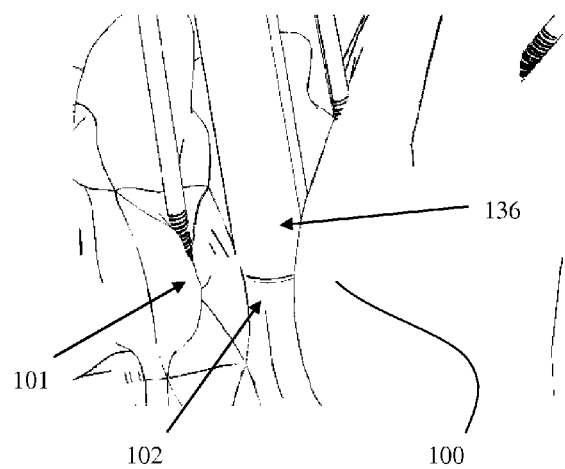
FIG. 71 is an enlarged oblique view of a bone graft impactor inserted into an SI joint, with a working channel removed from view for clarity.

FIGS. 55-57 illustrate a process of stabilizing the exposure device within incision. As depicted, the exposure device is stabilized using fixing pins 126, slotted through fixing pin holes or slots 139 on sides of the first and second working channels 239 and 240. Fixing pins 126 may have any suitable structure that permit them to stabilize the exposure device. In some embodiments, stabilizing pins 126 can penetrate the skin and/or flesh and tissue of a human. It is to be appreciated that any suitable method of stabilizing exposure device may be used. Dilator 116 and guide pin 115 may be removed from the first working channel either before or after the fixing pins 126 are inserted.

Guide pins 115 may be inserted into the incision through the first and second working channels 239 and 240, either through the dilator before it is removed, or through a guide sleeves that are used to insert the guide pins 115 and then are removed from the first and second working channels 239 and 240.

FIGS. 59-60 illustrate insertion of drill bit apparatus 122 into the incisions through the first and second working channels 239 and 240 of the exposure device. The drill bit may be connected to a power drill configured for medical procedures. The drill bit apparatus 122 may have cylindrical outer walls that allow the drill bit apparatus to freely spin with the hollow barrel of the first and second working channels 239 and 240. The cylindrical outer wall may comprise a low-friction material that facilitates smooth spinning of the drill within the hollow barrels of the first and second working channels. The proximal ends of the drill bit apparatus 122 may be inserted into the first and second working channels 239 and 240 and may be advanced to a predetermined point. In some examples, the proximal ends of drill bit apparatus 122 do not extend past the proximal end of the first and second working channels 239 and 240 when fully inserted. Preferably, drill bit apparatus 122 are configured such that it will interact with the first and second working channels 239 and 240 only in an orientation that ensures proper positioning of drill bit apparatus 122 relative to the SI joint and the ilium. For example, the drill bit apparatus may fit snugly into the hollow barrel to avoid any axial deviations, but may still be able to spin freely and at a rapid rotational speed without causing excessive friction or causing significant extraneous or unwanted motion.

The drill bits in the drill bit apparatus 122 may be advanced into channel the first and second working channels 239 and 240. With regard to the drill in the first working channel 239, the drill bit is advanced toward SI joint to a predetermined depth. This may be accomplished by an arrestor system in the drill that only allows a particular depth of insertion or by any other suitable method. The drill bit in the first working channels 239 may be positioned such that when activated it will create a void in the patient's SI joint by displacing portions of sacrum and ilium. In such examples, the drill bit may be configured such that it will contact the patient's SI joint at a desired portion of the joint and, once activated, will create a void of a desired depth.

Figure 33:
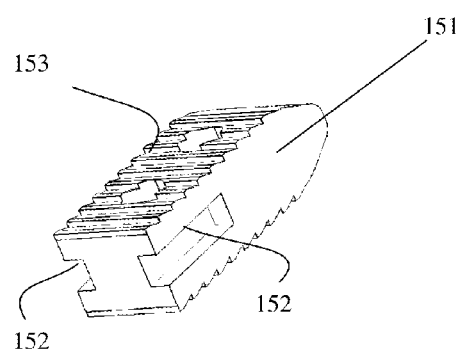
FIG. 33 is a perspective view of a fusion implant or bone graft implant.
Figure 34:
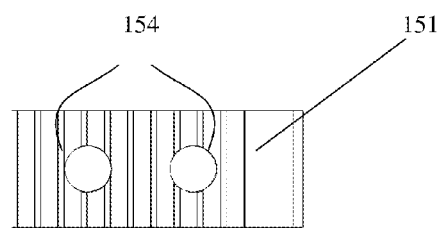
FIG. 34 is a top view of the fusion implant or bone graft implant.
Figure 35:
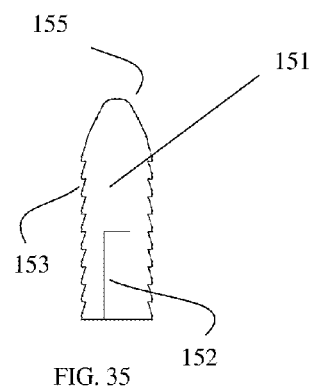
FIG. 35 is a side view of the fusion implant or bone graft implant.

The void may be configured to receive a void for receiving a graft (e.g., a bone graft) or a joint repairing appliance or apparatus for fusing the SI joint. Other joint repairing appliances or apparatus may include a polyether ether ketone (PEEK) implant, a titanium implant, an implant comprising a biological material other than bone, etc. These additional implants may have a shape and features like the implant 151 shown in FIGS. 33-35. These additional implant materials. As an example and without limiting the invention, the implant may be a bone graft as shown in FIGS. 33-35. The implant 151 may be substantially rectangular, having ribbing 153 on opposing sides to create a surface for catching or gripping with the SI joint when it is inserted. The implant 151 may also have a tapered proximal end to be inserted into the SI joint to act as a wedge, facilitating insertion. The implant 151 may also have slots 152 for receiving forceps of an inserter, and transverse holes to allow bone tissue to grow through the implant and incorporate the implant into the native bone tissue, thereby fusing the SI joint.

The drill bit in the second working channels 239 may be positioned such that when activated it will create drill a hole through the iliac wing of the patient near the iliac crest and through the sacrum, specifically the S1 vertebra. The drill bit may have sufficient length to reach the S1 vertebra from the iliac wing position of the second working channel. The relative angled position of the first and second working channels 239 and 240 of the exposure device positions the second working channel such that the drill bit can be advanced through to the S1 vertebra without traversed the SI joint, thereby avoiding any damage to the SI joint tissues (e.g., the ligaments).

As shown in FIGS. 66-71, several implements may be inserted through the first working channel 239 into the void in the SI joint to prepare the void for receiving a bone graft. For instance, a box chisel 131 and or a rasp 132 may be inserted into the void through the first working channel 239 to expand and clear tissue from the void to facilitate a clean and efficient insertion of the bone graft into the void. An impactor 136 may also be used to deepen or spread the void.

Figure 36:
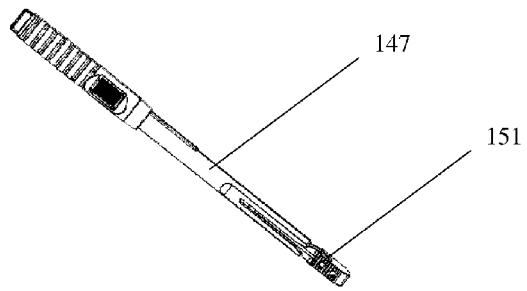
FIG. 36 is a perspective view of a fusion implant or bone graft inserter assembly for use with a surgical tool according to an embodiment of the present invention.
Figure 37:
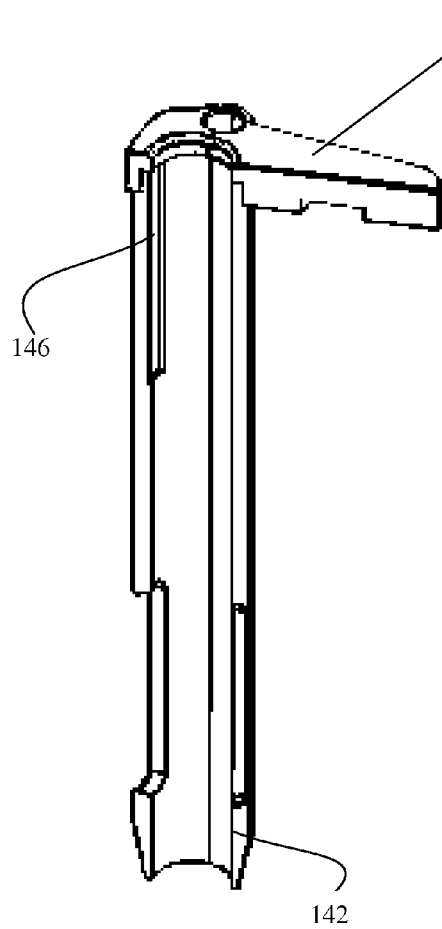
FIG. 37 is a cross sectional view of one barrel of a surgical tool according to an embodiment of the present invention.
Figure 38:
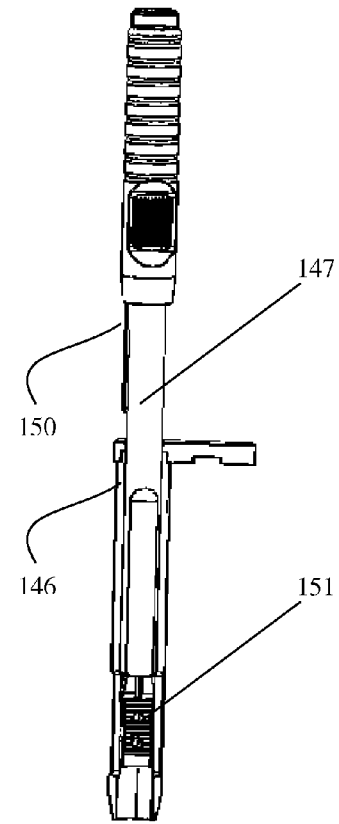
FIG. 38 is a cross sectional, side view of one barrel a surgical tool according to an embodiment of the present invention engaged with a fusion implant or bone graft assembly.
Figure 39:
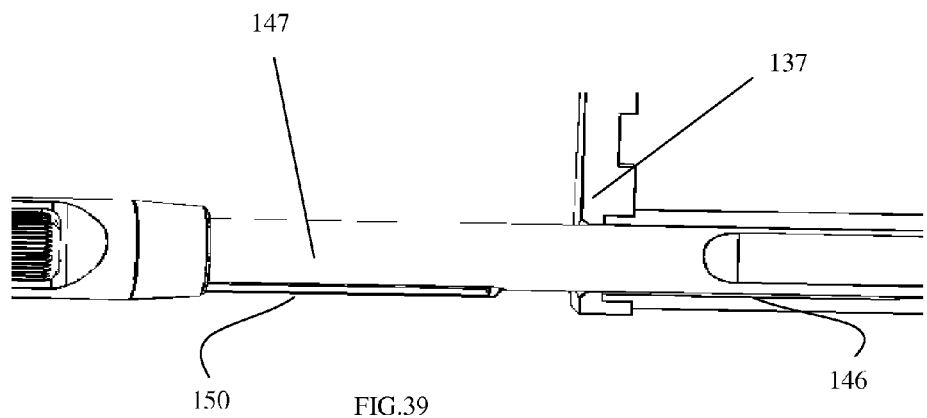
FIG. 39 is a cross sectional, side view of one barrel a surgical tool according to an embodiment of the present invention engaged with a fusion implant or bone graft assembly.
Figure 40:
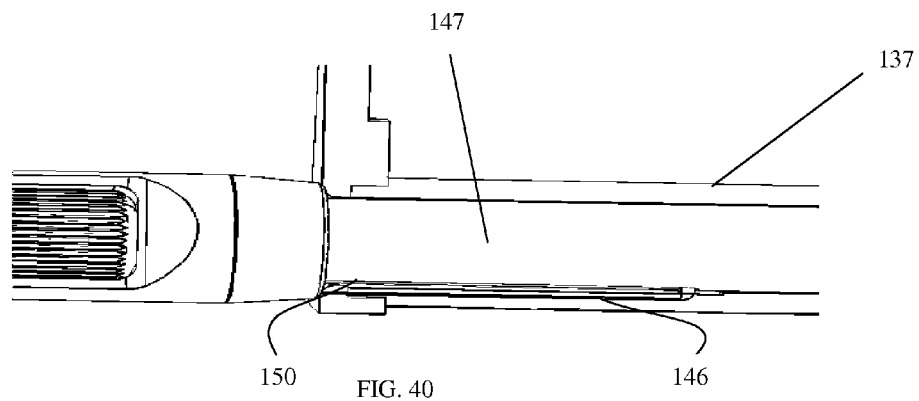
FIG. 40 is a cross sectional, side view of one barrel a surgical tool according to an embodiment of the present invention fully engaged with a fusion implant or bone graft assembly.
Figures 41, 42, 43:
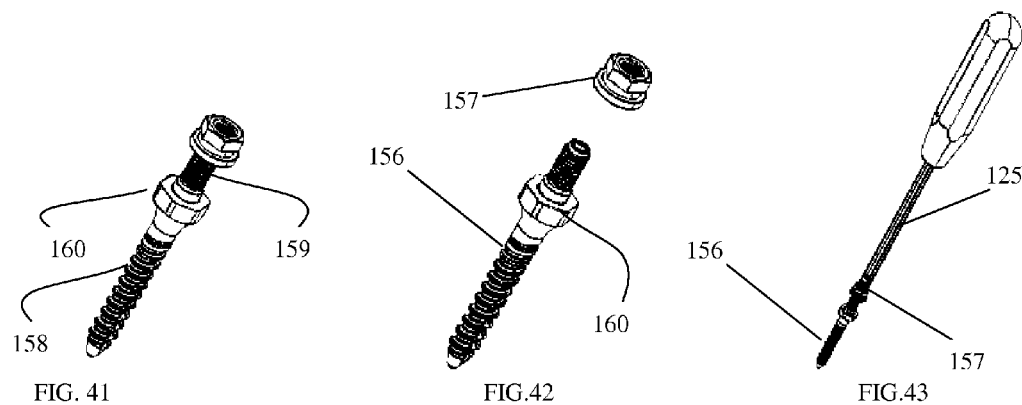
FIG. 41 is a perspective view of a fixation implant assembly.
FIG. 42 is an exploded, perspective view of a fixation implant assembly.
FIG. 43 is a perspective view of a fixation implant insertion assembly.
Figures 44, 45:
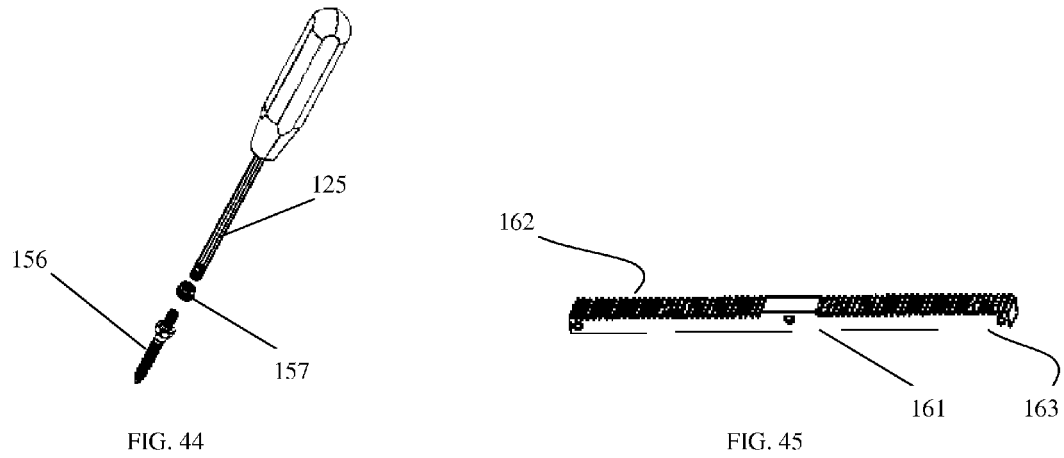
FIG. 44 is an exploded, perspective view of a fixation implant insertion assembly.
FIG. 45 is a perspective view of an adjustable rack for attaching working channels according to an embodiment of the present invention.
Figure 46:
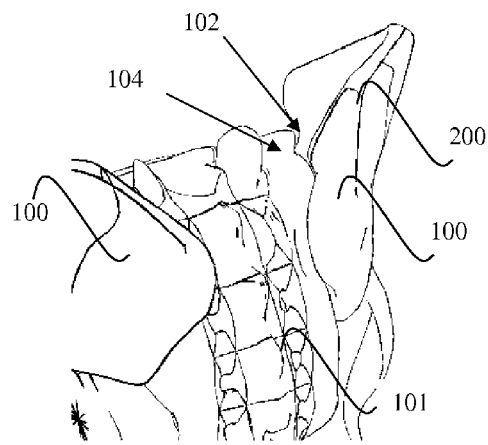
FIG. 46 is an oblique view of the sacroiliac joint.
Figure 47:
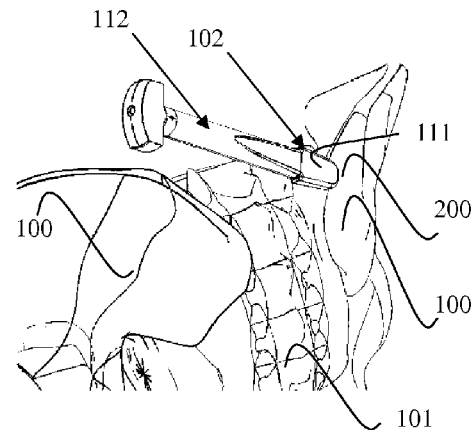
FIG. 47 is an oblique view of the sacroiliac joint and a joint probe.
Figure 48:
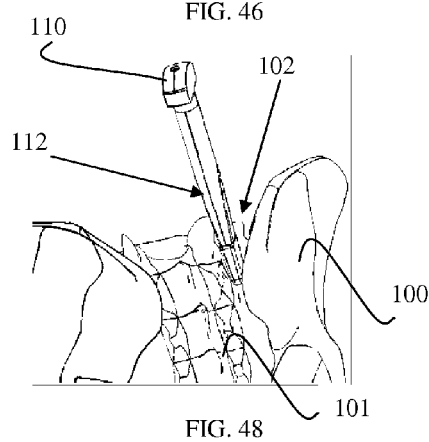
FIG. 48 is an oblique view of the sacroiliac joint and a joint probe with the joint probe identifying the SI joint.
Figure 49:
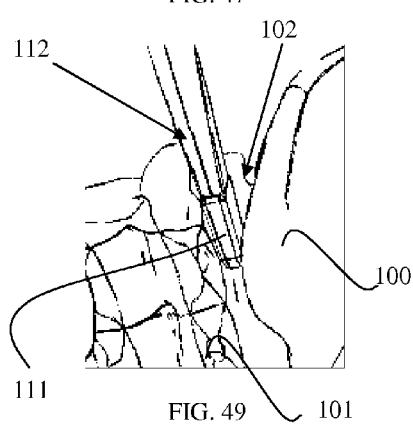
FIG. 49 is an enlarged oblique view of the sacroiliac joint and a joint probe with the joint probe identifying the SI joint.
Figure 50:
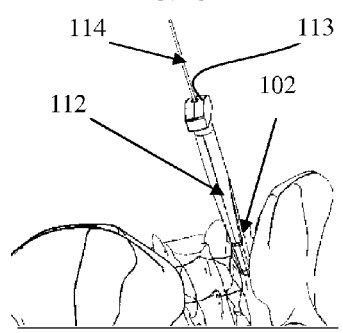
FIG. 50 is an oblique view of the SI joint and a joint probe with a guide pin marking the SI joint.
Figure 51:
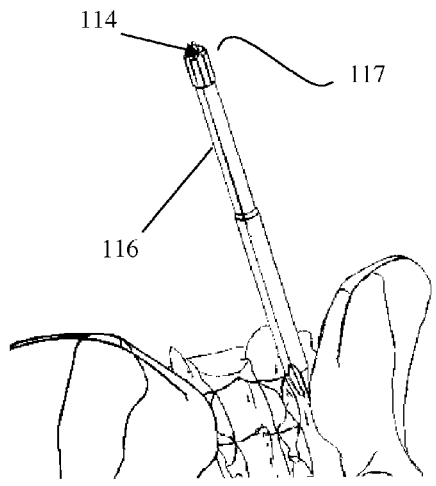
FIG. 51 is an oblique view of an SI joint with a joint cutting instrument entering the joint.
Figure 52:
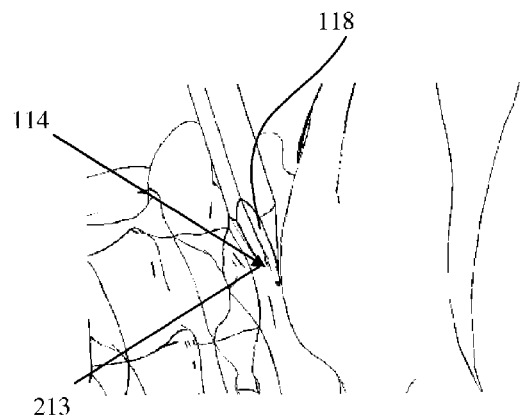
FIG. 52 is an enlarged oblique view of an SI joint with a joint cutting instrument entering the joint.
Figures 72, 73:
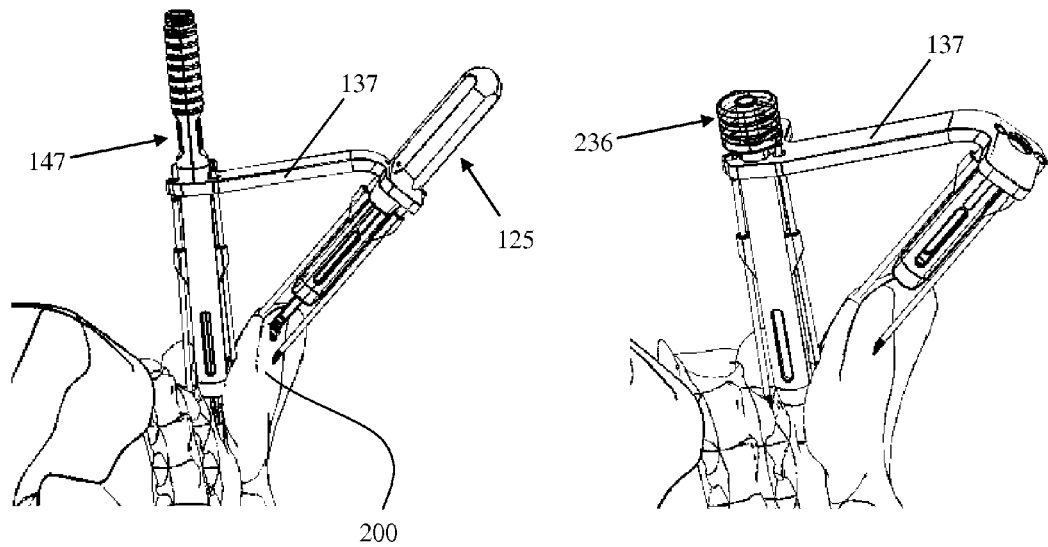
FIG. 72 is an oblique view of a surgical tool according to an embodiment of the present invention inserted into an SI joint with a fusion implant or bone graft inserter assembly inserted into a working channel of the surgical tool and a fixation device inserter assembly inserted into another working channel of the surgical tool.
FIG. 73 is an oblique view of a surgical tool according to an embodiment of the present invention inserted into an SI joint with a secondary bone graft impactor inserted into a working channel of the surgical tool.
Figure 74:
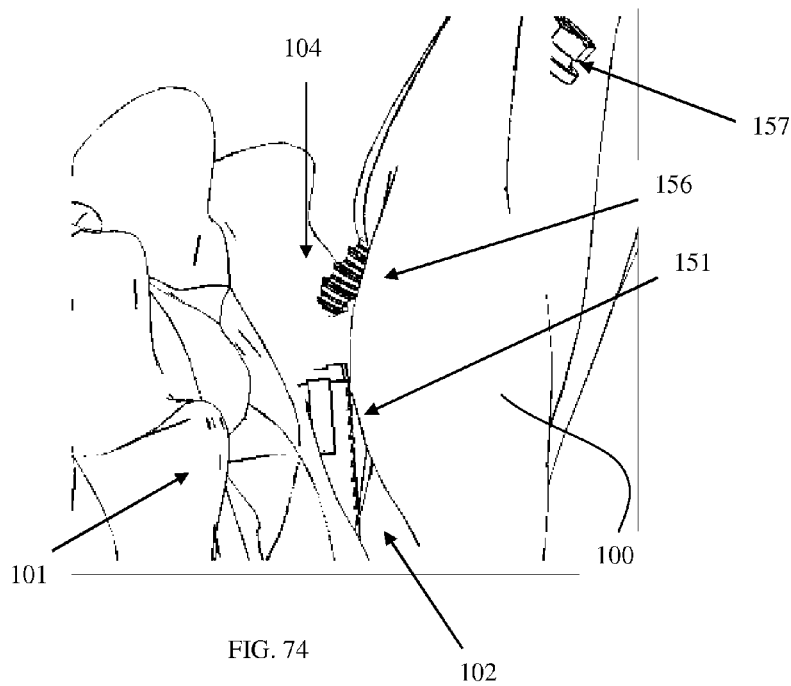
FIG. 74 is an enlarged, oblique view of a fusion implant and a fixation implant of in place.
Figure 75:
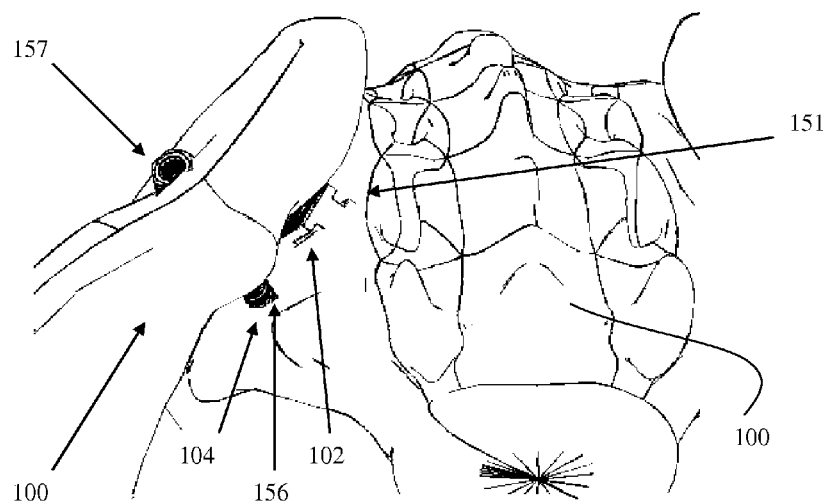
FIG. 75 is an enlarged, superior view of a fusion implant and a fixation implant of in place.

FIGS. 36 and 72 illustrates the use of a fusion implant inserter 147 to insert a an implant 151 (e.g., a bone graft) into the void in the SI joint. The inserter 147 may be inserted into the first working channel 239 of the exposure device. Prior to insertion, the implant 151 is grasped by the forceps of the inserter 147, which engage with grooves 152 along sides of the implant 151. The inserter 147 with implant 151 engaged therewith is inserted into the first working channel and may be advanced until it meets resistance at the void. The inserter 147 may then release the implant 151, leaving it in the void. In some examples, the inserter 147 may have a mechanism for grasping and releasing the implant 151, providing an efficient means of depositing the implant 151 in the void.

Subsequently, an impactor 236 may be used to exert force on the implant 151 as it is in the void, in order to drive graft 151 securely into the void, as shown in FIG. 73. The implant 151 may thereby be properly inserted into the void. Additionally, the impactor 236 may be used to add additional therapeutic materials, such as bone morphogenetic proteins (BMP), demineralized bone matrix (DBM), stem cells, and other materials, to the void to improve recovery and growth of the bone in the SI joint.

A joint fusion device (e.g., a bone screw) may be inserted into the iliac wing and the sacrum (the S1 vertebra) through the second working channel as the double-barreled exposure device is secured to the SI joint and the ilium. The fusion device 157 may be inserted at angle into the ilium and the sacrum that compresses the SI joint, thereby compressing the implant 151 with the SI joint. However, in other embodiments the angle of the hole drilled in the ilium and sacrum in an orientation that distracts the SI joint, providing room in the SI joint for bone tissue grow around the implant. In further embodiments, the structure of the joint fusion device 157 may be configured to create distraction in the SI joint.

The fusion device 157 may be inserted into the second working channel along with a fusion implant device 125 engaged therewith. In the case of a screw, the screw 157 may be advanced into the hole drilled through the ilium and the sacrum manually with a specialized driver. Alternatively, the screw or other fusion device can be installed by an automated process.

Subsequently, the fusion implant device and the double-barreled exposure device may be removed from the patient. Also, the fixing pins 126 may be removed and the exposure device may be removed from both incisions. The tissues in the incisions may then be sutured, to facilitate healing.

Figure 76:
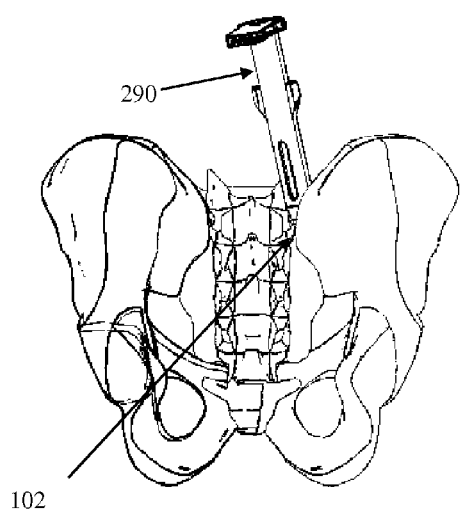
FIG. 76 is a posterior view of a pelvis with a surgical tool according to an embodiment of the present invention inserted into an SI joint.
Figure 77:
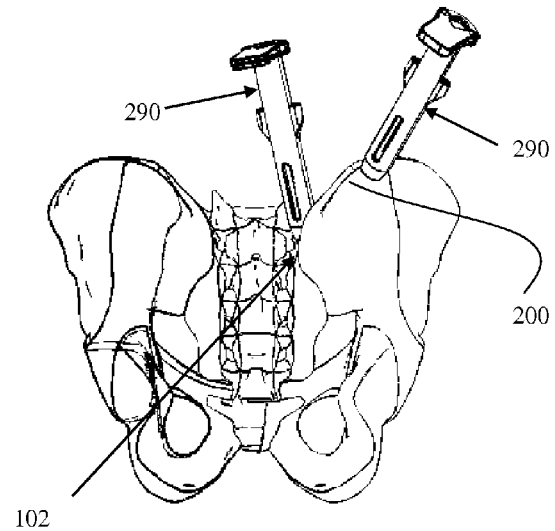
FIG. 77 is a posterior view of a pelvis with a surgical tool according to an embodiment of the present invention with two independent working channels, one inserted into an SI joint and one inserted over an iliac crest.
Figure 78:
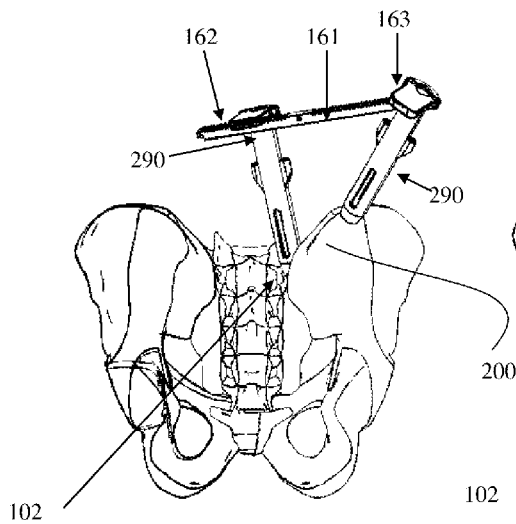
FIG. 78 is a posterior view of a pelvis with a surgical tool according to an embodiment of the present invention with two independent working channels attached by an adjustable rack.
Figure 79:
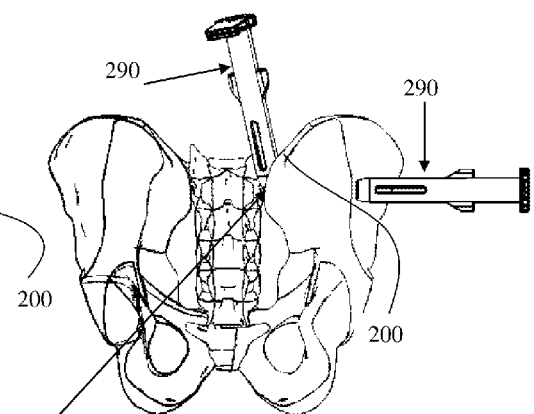
FIG. 79 is a posterior view of a pelvis with a surgical tool according to an embodiment of the present invention with two independent working channels, one inserted into an SI joint and one inserted over an iliac crest.

In some embodiments, the working channels may have different structures and orientations. Without limiting the invention, FIGS. 76-81 illustrate further embodiments of the invention. In FIG. 76, a single working channel 290 is shown engaged with the SI joint. In this example, the single working channel 290 can be individually orientated and engaged with the SI joint, and separately as second working channel 290 may be engaged with the preferred insertion point on the ilium, as shown in FIG. 77. This embodiment provides the flexibility of individually orienting the two working channels. Subsequently, an adjustable rack 161 may be engaged with both the of the individual working channels 290 as shown in FIG. 78, thereby stabilizing the two working channels and maintaining their orientation relative to one another. It is to be appreciated that the two working channels in this example may be stabilized by other or additional methods.

Figure 80:
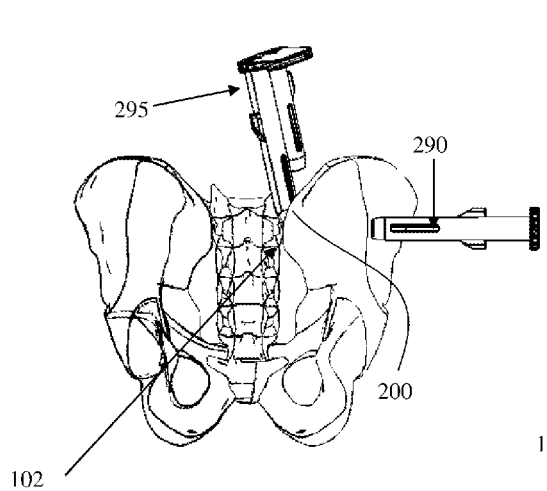
FIG. 80 is a posterior view of a pelvis with a surgical tool according to an embodiment of the present invention with two independent working channels, one inserted into an SI joint and one inserted over an iliac crest. The working channel inserted into the SI joint may have two barrels for the placement of two fusion devices in the SI joint.
Figure 81:
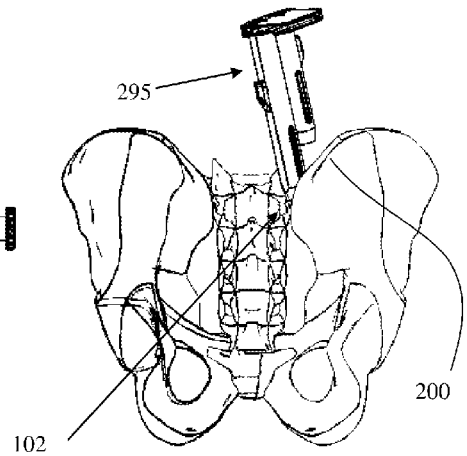
FIG. 81 is a posterior view of a pelvis with a surgical tool according to an embodiment of the present invention with two barrels for the placement of two fusion devices.
Figure 88:
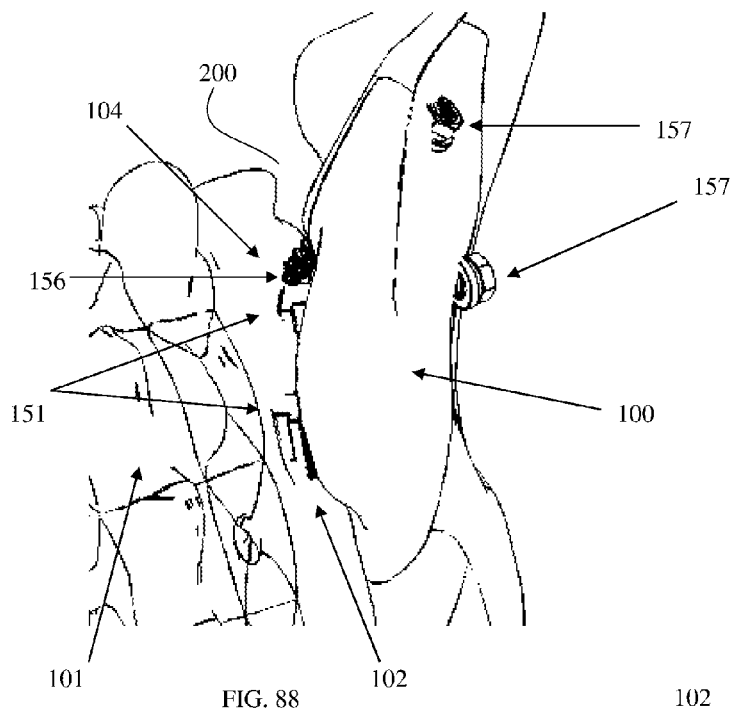
FIG. 88 is oblique, posterior view showing two fixation devices in an ilium and sacrum and two fusion device in an SI joint according to an embodiment of the present invention.
Figure 89:
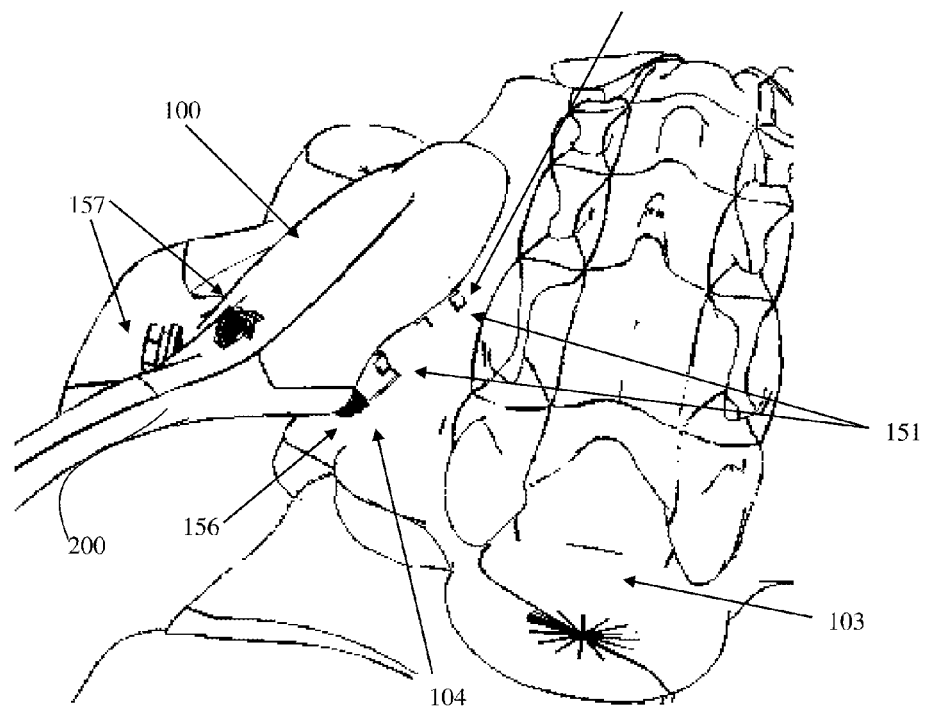
FIG. 89 is a superior view showing two fixation devices in an ilium and sacrum and two fusion device in an SI joint according to an embodiment of the present invention.

In some embodiments, the working channel may have two barrel or more barrels (e.g., 3, 4, or more barrels, in various orientations—parallel, skewed, etc.), each capable of receiving surgical implements and being used to introduce implants or other devices or materials into the SI joint. For instance, the two or more barrels may include two parallel barrels, two skewed barrels, three parallel barrels in a single plane, three parallel barrels in a triangular arrangement, etc. As an example, and without limiting the invention, FIG. 80 shows an individual working channel 295 engaged with the SI joint having two parallel barrels. The additional barrel may facilitate the formation of a void and the insertion of a second implant (e.g., bone graft) or some other fusion device in the second void. The working channel 295 may be used individually in a SI joint fusion procedure, or in combination with another working channel. For example, and without limiting the invention, the working channel 290 can be used in conjunction with the working channel 295, allowing for insertion of a joint fusing device in the ilium and sacrum. The working channels 290 and 295 may also be connected to one another by an adjustable rack, as described above, thereby stabilizing the two working channels and maintaining their orientation relative to one another. It is to be appreciated that working channels having two or more barrels may fixedly attached to a second working channel at an angle by a connecting member, as described in the examples above.

It is also to be appreciated that the individual working channel having two or more barrels are not limited to SI joint fusion procedures, and may have other beneficial applications. Furthermore, the other working channel apparatuses may be useful in other procedures as well. For instance, the working channels of the present invention may be associated with various racks (e.g., having varying lengths and means of attachment) that facilitate procedures where two difficult surgical sites are needed.

It is to be further appreciated that the working channel apparatuses (exposure devices) described herein can be utilized in SI joint fusion procedures on both SI joints of a patient simultaneously. As shown in FIG. 82, the presently described exposure devices can be utilized in a bilateral SI joint procedure.

The methods described herein may be used to treat both of the patient's SI joints either at the same or approximately the same time (e.g., during the same procedure) or in sequence.

It is to be understood that variations and modifications of the present invention may be made without departing from the scope thereof. It is also to be understood that the present invention is not to be limited by the specific embodiments disclosed herein, but only in accordance with the appended claims when read in light of the foregoing specification.

What is claimed:

1. A method for repairing a sacroiliac joint of a patient, comprising:
   a. creating a first incision in the patient's skin proximal to said sacroiliac joint;
   b. creating a second incision in the patient's skin over the patient's ilium adjacent to said sacroiliac joint;
   c. inserting a first working channel into said first incision;
   d. inserting a second working channel into said second incision, wherein said first working channel and said second working channel are connected;
   e. creating a void in said sacroiliac joint using a tool inserted into said sacroiliac joint through said first working channel;
   f. inserting an implant into said void through said first working channel; and
   g. inserting a joint fusing device into said ilium and the patient's sacrum through said second working channel, wherein said joint fusing device does not traverse said sacroiliac joint.

2. The method of claim 1, wherein said first and second working channels are connected by a connecting bar.

3. The method of claim 2, wherein said connecting bar has a bend therein, said bend is configured to accommodate contour of the pelvis between the ilium and the sacroiliac joint such that said first working channel can be engaged with a posterior side of the sacroiliac joint and said second working channel can be engaged with a posterior portion of an iliac wing of the ilium simultaneously.

4. The method of claim 1, wherein an orientation of said second working channel relative to said first working channel positions said second working channel over an iliac wing of said ilium when said first working channel is engaged with said sacroiliac joint, and a longitudinal axis of said second working channel does not intersect said sacroiliac joint when said first working channel is engaged with said sacroiliac joint.

5. The method of claim 2, wherein said connecting bar has a bend therein, and said bend positions second working channel at an acute angle relative to said first working channel.

6. The method of claim 1, wherein said first working channel has a rounded, tapered end configured to be inserted directly into said sacroiliac joint, said round end operable to distract said sacroiliac joint.

7. The method of claim 1, wherein a longitudinal axis of said second working channel does not intersect said sacroiliac joint when said second working channel is inserted into said second incision and said first working channel is inserted into said first incision.

8. The method of claim 1, further comprising inserting a drill into said second working channel and drilling a hole through an iliac wing and into said sacrum, wherein said hole does not traverse said sacroiliac joint and said joint fusing device is inserted into the iliac wing of said ilium and said sacrum.

9. The method of claim 1, wherein the implant contacts said ilium and said sacrum and the joint fusing device compresses the sacroiliac joint, thereby securing said implant in the sacroiliac joint.

10. The method of claim 9, wherein the implant is configured to substantially fuse the patient's ilium to the patient's sacrum, thereby substantially immobilizing the patient's sacroiliac joint.

11. The method of claim 1, further comprising inserting a guide wire into said sacroiliac joint through said first incision, slotting a joint cutting tool over said guide wire, and placing said first working channel over said guide wire and said joint cutting tool, such that said guide wire and joint cutting tool are within a hollow barrel of said first working channel and an end of said working channel is within said first incision.

12. The method of claim 1, wherein said tool is a drilling device and creating said void comprises inserting a drill bit into a hollow barrel of said first working channel, and activating a drilling device, thereby drilling said void in said sacroiliac joint, wherein said drill bit passes between the articular surfaces of said sacroiliac joint.

13. The method of claim 1, further comprising attaching said first working channel to said second working channel with an adjustable rack.

14. The method of claim 1, further comprising securing said first working channel in said first incision by inserting at least one pin through a slot on exterior of said first working channel and into the patient.

15. The method of claim 1, further comprising securing said second working channel in said second incision by inserting at least one pin through a slot on exterior of said second working channel and into the patient.

16. The method of claim 1, wherein inserting said implant into said void comprises:
   a. attaching the implant to an inserter, wherein the inserter has a proximal end configured to attach to the implant;
   b. inserting the inserter into a hollow barrel of said first working channel until a guide slot within said hollow barrel and engaged with said inserter prevents the inserter from moving further into said sacroiliac joint; and
   c. inserting an impactor into the hollow barrel of said first working channel until the impactor contacts the implant and securely positions the implant in the void.

17. The method of claim 1, wherein the implant is substantially rectangular and has a proximal end and a distal end, wherein the proximal end of the implant is tapered.

18. The method of claim 17, wherein the implant has ribbing on at least one side.

19. The method of claim 1, wherein the implant contacts the patient's ilium and the patient's sacrum and the joint fusing device distracts the sacroiliac joint.

20. The method of claim 1, wherein said first working channel comprises a first barrel and a second barrel, wherein said implant is inserted into said void through said first barrel.

21. The method of claim 20, further comprising forming a second void in said sacroiliac joint and inserting a second implant into said second void through said second barrel.

22. A method for repairing a sacroiliac joint of a patient, comprising:
   a. creating a first incision in the patient's skin proximal to the patient's sacroiliac joint;
   b. creating a second incision in the patient's skin over the patient's ilium adjacent to said sacroiliac joint;
   c. inserting a surgical channel tool into said first incision and said second incision, said surgical channel tool having a first working channel inserted into said first incision and a second working channel inserted into said second incision;
   d. inserting an implant into said sacroiliac joint through said first working channel; and
   e. inserting a joint fusing device into said ilium and said sacrum through said second working channel, wherein said joint fusing device does not traverse said sacroiliac joint.

23. The method of claim 22, wherein said first and second working channels are connected by a connecting bar and held at an acute angle relative to each other.

24. The method of claim 23, wherein said connecting bar has a bend therein.

25. The method of claim 23, wherein said acute angle simultaneously allows said first working channel to be engaged with a posterior side of said sacroiliac joint and said second working channel to be engaged with a posterior portion of an iliac wing of said ilium, wherein a longitudinal axis of said second working channel does not intersect said sacroiliac joint.

26. The method of claim 23, wherein said acute angle positions said second working channel over an iliac wing of said ilium such that a longitudinal axis of said second working channel does not intersect said sacroiliac joint when said first working channel is inserted into said first incision.

27. The method of claim 22, wherein said first working channel is inserted directly into said sacroiliac joint.

28. The method of claim 27, wherein an end of said first working channel inserted into said sacroiliac joint is round and is operable to distract said sacroiliac joint.

29. The method of claim 27, wherein an end of said first working channel inserted into said sacroiliac joint has a rounded and tapered profile.

30. The method of claim 22, further comprising inserting a drill into said second working channel and drilling a hole through an iliac wing of said ilium and into said sacrum, wherein said hole does not traverse said sacroiliac joint and said joint fusing device is inserted into said iliac wing and said sacrum of the patient through said hole.

31. The method of claim 22, wherein the implant contacts said ilium and said sacrum and the joint fusing device compresses the sacroiliac joint, thereby securing said implant in the sacroiliac joint.

32. The method of claim 22, further comprising creating a void in said sacroiliac joint between an articular surface of said ilium and an articular surface of said sacrum, including inserting a drill bit into a hollow barrel of said first working channel, and activating a drilling device, thereby drilling said void into the sacroiliac joint.

33. The method of claim 22, further comprising securing said first working channel in said first incision by inserting at least one pin through a slot on exterior of said first working channel and into the patient.

34. The method of claim 22, further comprising securing said second working channel in said second incision by inserting at least one pin through a slot on exterior of said second working channel and into the patient.

35. The method of claim 22, wherein the inserting the implant comprises:
   a. attaching the implant to an inserter, wherein the inserter has a proximal end configured to attach to the implant;
   b. inserting the inserter into a hollow barrel of said first working channel until a guide slot within said hollow barrel and engaged with said inserter prevents the inserter from moving further into said sacroiliac joint; and
   c. inserting an impactor into the hollow barrel until the impactor contacts the implant and securely positions the implant within the sacroiliac joint.

36. The method of claim 22, wherein the implant is substantially rectangular and has a proximal end and a distal end, wherein the proximal end of the implant is tapered.

37. The method of claim 36, wherein the implant has ribbing on at least one side.

38. The method of claim 22, wherein the implant comprises a bone graft.

39. The method of claim 22, wherein the implant contacts the patient's ilium and the patient's sacrum and the joint fusing device distracts said sacroiliac joint.

40. A method of implanting a joint fusion implant into a sacroiliac joint of a patient, comprising:
   a. creating a first incision in the patient's skin proximal to the patient's sacroiliac joint;
   b. creating a second incision over the patient's ilium adjacent to said sacroiliac joint;
   c. using a joint probe to identify the sacroiliac joint;
   d. inserting a guide wire through a canal in said joint probe and into said sacroiliac joint;
   e. slotting a surgical channel device over said guide wire, said surgical channel device having a first working channel directly inserted into said first incision and a second working channel directly inserted into said second incision, said first and second working channels being connecting by a connecting member, wherein said connecting member has a bend therein, and said bend positions second working channel such that a longitudinal axis of said second working channel does not intersect said sacroiliac joint;
   f. creating a void in said sacroiliac joint, wherein creating said void comprises displacing a portion of the patient's ilium and a portion of the patient's sacrum, inserting a drill bit through said first working channel and into said sacroiliac joint, and drilling said void into said sacroiliac joint;
   g. inserting an implant into said void through said first working channel, wherein said implant is configured to substantially fuse said ilium to the patient's sacrum;
   h. drilling a hole in said ilium and said sacrum, wherein drilling said hole comprises inserting a drill bit through said second working channel and activating a drill mechanism until the drill bit has entered said sacrum to a predetermined depth; and
   i. inserting a joint fusion device into said hole in said ilium and said sacrum, wherein said joint fusion device does not traverse said sacroiliac joint.

41. The method of claim 1, wherein said first working channel and said second working channel are held in position relative to one another.

42. The method of claim 1, wherein said void is created between an articular surface of said ilium and an articular surface of said sacrum.

43. The method of claim 1, wherein said joint fusing device is inserted into said ilium and said sacrum posteriorly to said sacroiliac joint.

44. The method of claim 1, wherein said first working channel comprises a guide slot in an interior thereof, and said guide slot is operable to limit rotation and insertion depths of surgical tools, including an implant inserter.

45. The method of claim 1, wherein said second working channel comprises a guide slot in an interior thereof, and said guide slot is operable to limit rotation and insertion depths of surgical tools, including a drill.

46. The method of claim 22, wherein said implant is inserted between an articular surface of said ilium and an articular surface of said sacrum.

47. The method of claim 22, wherein said joint fusing device is inserted into said ilium and said sacrum posteriorly to said sacroiliac joint.

48. The method of claim 22, wherein said first working channel comprises a guide slot in an interior thereof, and said guide slot is operable to limit rotation and insertion depths of surgical tools, including an implant inserter.

49. The method of claim 22, wherein said second working channel comprises a guide slot in an interior thereof, and said guide slot is operable to limit rotation and insertion depths of surgical tools, including a drill.

50. The method of claim 22, further comprising inserting a second implant into said sacroiliac joint, wherein said first working channel comprises a first barrel and a second barrel, and said implant is inserted into said sacroiliac joint through said first barrel and said second implant is inserted into said sacroiliac joint through said second barrel.

51. A method for repairing a sacroiliac joint of a patient using a surgical tool comprising a first working channel having a first hollow barrel, a second working channel having a second hollow barrel, and a connecting member connecting said first working channel to said second working channel, the method comprising:
   a. creating a first incision in the patient's skin proximal to said sacroiliac joint;
   b. creating a second incision in the patient's skin over the patient's ilium adjacent to said sacroiliac joint;
   c. inserting said first working channel into said first incision;
   d. inserting said second working channel into said second incision;
   e. creating a void in said sacroiliac joint using a tool inserted into said sacroiliac joint through said first working channel;
   f. inserting an implant into said void through said first working channel; and
   g. inserting a joint fusing device into said ilium and the patient's sacrum through said second working channel, wherein said joint fusing device does not traverse said sacroiliac joint, and
      wherein said connecting member has a bend therein configured to accommodate contour of the pelvis between an iliac wing and said sacroiliac joint.

52. The method of claim 51, wherein said first working channel has a rounded, tapered end configured to be inserted directly into said first incision to enable the insertion of various surgical instruments into said sacroiliac joint.

53. The method of claim 51, wherein the position of said second working channel over the iliac wing enables the insertion of said joint fusing device into said iliac wing and said sacrum without said joint fusing device traversing said sacroiliac joint.

54. The method of claim 51, wherein said connecting member is fixed to said first working channel and said second working channel.

55. The method of claim 51, wherein said connecting member comprises an adjustable rack that is detachable from said first working channel and said second working channel.

56. The method of claim 51, wherein said joint fusion device is operable to connect said iliac wing to said sacrum, and compress said sacroiliac joint therebetween, without traversing the sacroiliac joint.

57. The method of claim 51, wherein said first working channel comprises a guide slot in an interior of said first hollow barrel, said guide slot operable to limit rotation and an insertion depth of a surgical tool.

58. The method of claim 51, wherein said second working channel comprises a guide slot in an interior of said second hollow barrel, said guide slot operable to limit rotation and an insertion depth of a surgical tool.

59. The method of claim 51, wherein said first working channel comprises two hollow barrels.

60. The method of claim 51, wherein a longitudinal axis of said second working channel does not intersect said sacroiliac joint when said second working channel is inserted into said second incision and said first working channel is simultaneously inserted into said first incision.

61. The method of claim 51, further comprising inserting a drill into said second working channel and drilling a hole through the iliac wing and into said sacrum, where said hole does not traverse said sacroiliac joint and said joint fusing device is inserted into said hole through the iliac wing and said sacrum.

62. The method of claim 51, wherein said implant contacts said ilium and said sacrum and the joint fusing device distracts the sacroiliac joint.

63. The method of claim 51, wherein the implant is operable to substantially fuse said ilium to said sacrum, thereby substantially immobilizing said sacroiliac joint.

64. The method of claim 51, wherein inserting said implant into said void comprises:
   a. attaching the implant to an inserter, wherein the inserter has a proximal end operable to attach to the implant;
   b. inserting the inserter into a hollow barrel of said first working channel until a guide slot within said hollow barrel and engaged with said inserter prevents the inserter from moving further into said sacroiliac joint; and
   c. inserting an impactor into the hollow barrel of said first working channel until the impactor contacts the implant and securely positions the implant in the void.

* * * * *